(12) United States Patent
Kaznessis et al.

(10) Patent No.: US 11,965,190 B2
(45) Date of Patent: Apr. 23, 2024

(54) VECTORS, GENETICALLY MODIFIED BACTERIA, AND METHODS OF MAKING AND USING

(71) Applicant: REGENTS OF THE UNIVERSITY OF MINNESOTA, Minneapolis, MN (US)

(72) Inventors: Yiannis John Kaznessis, New Brighton, MN (US); Seth Ritter, Minneapolis, MN (US); Benjamin Hackel, Edina, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 348 days.

(21) Appl. No.: 16/645,281

(22) PCT Filed: Sep. 7, 2018

(86) PCT No.: PCT/US2018/049881
§ 371 (c)(1),
(2) Date: Mar. 6, 2020

(87) PCT Pub. No.: WO2019/051179
PCT Pub. Date: Mar. 14, 2019

(65) Prior Publication Data
US 2020/0299665 A1   Sep. 24, 2020
US 2021/0269786 A9   Sep. 2, 2021

Related U.S. Application Data

(60) Provisional application No. 62/555,962, filed on Sep. 8, 2017.

(51) Int. Cl.
*C12N 15/74* (2006.01)
*A61K 35/747* (2015.01)
(Continued)

(52) U.S. Cl.
CPC .......... *C12N 9/2462* (2013.01); *A61K 35/747* (2013.01); *C12N 1/20* (2013.01);
(Continued)

(58) Field of Classification Search
CPC ........ C12N 15/62; C12N 15/52; C12N 15/74; C12N 15/625; C12N 15/63; C12N 15/635; C12N 15/11
See application file for complete search history.

(56) References Cited

U.S. PATENT DOCUMENTS

2015/0050717 A1* 2/2015 Collins .................... C12N 7/00
435/235.1
2015/0265660 A1    9/2015 Kaznessis et al.
(Continued)

FOREIGN PATENT DOCUMENTS

EP      2143729         1/2010
EP      2143729 A1 *    2/2010
KR      20160125639 A * 11/2016

OTHER PUBLICATIONS

Map of pQE plasmid, downloaded Apr. 1, 2022 from: https://www.qiagen.com/us/products/discovery-and-translational-research/protein-purification/tagged-protein-expression-purification-detection/n-terminus-pqe-vector-set/ (Year: 2022).*
(Continued)

*Primary Examiner* — Allison M Fox
*Assistant Examiner* — Qing Xu
(74) *Attorney, Agent, or Firm* — Mueting Raasch Group

(57) ABSTRACT

Provided herein are a vector, a genetically modified bacterium including the vector, methods of making the bacterium, methods of using the bacterium, and kits including the bacterium. The vector includes a coding region encoding at
(Continued)

least one antimicrobial peptide, and the antimicrobial peptide includes at least one lysin.

5 Claims, 7 Drawing Sheets

Specification includes a Sequence Listing.

(51) Int. Cl.
  C12N 1/20 (2006.01)
  C12N 9/36 (2006.01)
  C12N 15/62 (2006.01)
  C12N 15/63 (2006.01)
(52) U.S. Cl.
  CPC .......... *C12N 15/62* (2013.01); *C12N 15/635* (2013.01); *C12N 15/74* (2013.01); *C12N 15/746* (2013.01); *C12Y 302/01017* (2013.01)

(56) References Cited

U.S. PATENT DOCUMENTS

2016/0279175 A1* 9/2016 Kaznessis ............ C07K 14/315
2020/0068910 A1* 3/2020 Kazanaviciute ....... A61K 38/47

OTHER PUBLICATIONS

Written opinion of ISA, PCT/US2018/049881 filed on Sep. 7, 2018, of the instant application. (dated Year: 2019).*
Sanders et al., Appl. Environ. Microbiol., 1997, 63: 4877-4882 (Year: 1997).*
Sanders-2 et al., Mol. Microbiol., 1998, 27: 299-310 (Year: 1998).*
Loessner et al., Microbes and Infection, 2009, 11: 1097-1105 (Year: 2009).*
Borrero et al., Modified lactic acid bacteria detect and inhibit multiresistant enterococci. ACS Synth Biol 4, 299-306 (2015).
Borysowski et al., Bacteriophage endolysins as a novel class of antibacterial agents. Exp Biol Med (Maywood) 231, 366-377 (2006).
Casewell et al., The European ban on growth-promoting antibiotics and emerging consequences for human and animal health. J Antimicrob Chemother 52, 159-161 (2003).
Consumer Reports: Meat on Drugs: The overuse of antibiotics in food animals & what supermarkets and consumers can do to stop it, 2012, available on the world wide web at consumersunion.org/wp-content/uploads/2012/06/CR_Meat_On_Drugs_Report_06-12.pdf.
FDA, #209 Guidance for Industry The Judicious Use of Medically Important Antimicrobial Drugs in Food-Producing Animals, World Health Organization, Global action plan on antimicrobial resistance, 2015, ISBN: 9789241509763, Available at http://www.fda.gov/AnimalVeterinary/SafetyHealth/AntimicrobialResistance/, available at least as early as Feb. 14, 2017.
Fernandez et al., Enhanced secretion of biologically active murine interleukin-12 by Lactococcus lactis. Appl Environ Microbiol 75, 869-871 (2009).
Finn et al., HMMER web server: 2015 update. Nucleic Acids Res 43, W30-38 (2015).
Forkus et al., Antimicrobial Probiotics Reduce Salmonella enterica in Turkey Gastrointestinal Tracts. Sci Rep 7, 40695 (2017).
Fox et al., Campylobacter jejuni infection in the ferret: an animal model of human campylobacteriosis. Am J Vet Res 48, 85-90 (1987).
Geldart et al., Characterization of Class IIa Bacteriocin Resistance in Enterococcus faecium. Antimicrob Agents Chemother, 61(4):e02033-16 (2017).
Geldart et al., Chloride-Inducible Expression Vector for Delivery of Antimicrobial Peptides Targeting Antibiotic-Resistant Enterococcus faecium. Appl Environ Microbiol 81, 3889-3897 (2015).
Geldart et al., pMPES: A Modular Peptide Expression System for the Delivery of Antimicrobial Peptides to the Site of Gastrointestinal Infections Using Probiotics. Pharmaceuticals (Basel) 9(4):60. (2016).
Genbank Accession No. ADJ60177.
Genbank Accession No. ZP_02630819.
Gervasi et al., Application of Lactobacillus johnsonii expressing phage endolysin for control of Clostridium perfringens. Lett Appl Microbiol 59, 355-361 (2014).
Glenn et al., Analysis of antimicrobial resistance genes detected in multidrug-resistant Salmonella enterica serovar Typhimurium isolated from food animals. Microb Drug Resist 17, 407-418 (2011).
Glisson et al., Comparative efficacy of enrofloxacin, oxytetracycline, and sulfadimethoxine for the control of morbidity and mortality caused by Escherichia coli in broiler chickens. Avian Dis 48, 658-662 (2004).
Global action plan on antimicrobial resistance, World Health Organization, Publication date: 2015, ISBN: 9789241509763, Available online at http://www.who.int/antimicrobial-resistance/publications/global-action-plan/en/ , available at least as early as Feb. 14, 2017. (Reference Not Available).
Guiziou et al., A part toolbox to tune genetic expression in Bacillus subtilis. Nucleic Acids Res 44, 7495-7508 (2016).
Hopf et al., Mutation effects predicted from sequence co-variation. Nat Biotechnol 35, 128-135 (2017).
Humphrey et al., Experimental infection of hamsters with Campylobacter jejuni. J Infect Dis 151, 485-493 (1985).
International Preliminary Report on Patentability for PCT/US18/49881 dated Mar. 19, 2020, 12 pages.
International Search Report and Written Opinion for PCT/US18/49881 dated Jan. 28, 2019, 16 pages.
Jacob et al., Antimicrobial susceptibility of foodborne pathogens in organic or natural production systems: an overview. Foodborne Pathog Dis 5, 721-730 (2008).
Joint FAO/WHO/OIE Expert Meeting on Critically Important Antimicrobials, Rome, Italy, Nov. 2007, http://www.who.int/foodborne_disease/resources/Report_CIA_Meeting.pdf.
Karon et al., Human multidrug-resistant Salmonella Newport infections, Wisconsin, 2003-2005. Emerg Infect Dis 13, 1777-1780 (2007).
Kesmodel, "Meat Companies Go Antibiotics-Free as More Consumers Demand It," Wall Street Journal, Nov. 3, 2014. wsj.com/articles/ meat-companies-go-antibiotics-free-as-more-consumers-demand-it-1415071802.
Khachatourians, Agricultural use of antibiotics and the evolution and transfer of antibiotic-resistant bacteria. CMAJ 159, 1129-1136 (1998).
Lovland et al., Severely impaired production performance in broiler flocks with high incidence of Clostridium perfringens-associated hepatitis. Avian Pathol 30, 73-81 (2001).
Lungu et al., Listeria monocytogenes: antibiotic resistance in food production. Foodborne Pathog Dis 8, 569-578 (2011).
Mcclintock et al., Enterocin A mutants identified by saturation mutagenesis enhance potency towards vancomycin-resistant Enterococci. Biotechnol Bioeng 113, 414-423 (2016).
Mcdevitt, et al., Acamovic, T. & Sparks, N. H. C. Necrotic enteritis; a continuing challenge for the poultry industry. Worlds. Poult. Sci. J. 62, 221 (2006).
McDonald's statement on antibiotic use, Available online at http://news.mcdonalds.com/us/media-statements/response-to-antibiotics-in-chicken, available at least as early as Feb. 14, 2017. (Reference Not Available).
Mcewen et al., Antimicrobial use and resistance in animals. Clin Infect Dis, 34:Suppl 3; S93-S106 (2002).
Mellon, et al. Hogging it! Estimates of antimicrobial abuse in livestock. Union of Concerned Scientists, 2001. Available at www.ucsusa.org/publications.
Miller et al., Bacteriophage therapy for control of necrotic enteritis of broiler chickens experimentally infected with Clostridium perfringens. Avian Dis 54, 33-40 (2010).
Molbak et al., An outbreak of multidrug-resistant, quinolone-resistant Salmonella enterica serotype typhimurium DT104. N Engl J Med 341, 1420-1425 (1999).
M'Sadeq et al., Towards the control of necrotic enteritis in broiler chickens with in-feed antibiotics phasing-out worldwide. Anim Nutr 1, 1-11 (2015).

(56) References Cited

OTHER PUBLICATIONS

Natalia Clostridial Necrotic Enteritis in Poultry, Indonesian Bulletin of Animal and Verterinary Sciences, 14(4):133-142 (2004)—Abstract in English.
National Chicken Council Statistics, "Per Capita Consumption of Poultry and Livestock, 1965 to Forecast 2022, in Pounds" Obtained online at nationalchickencouncil.org/about-the-industry/statistics/per-capita-consumption-of-poultry-and-livestock-1965-to-estimated-2012-in-pounds/ Available at least as early as Feb. 14, 2017.
Ng et al., Engineering signal peptides for enhanced protein secretion from Lactococcus lactis. Appl Environ Microbiol 79, 347-356 (2013).
No antibiotics ever. Chick-fil-a's commitment, Available at https://thechickenwire.chick-fil-a.com/Inside-Chick-fil-a/No-Antibiotics-Ever-Chick-fil-As-Commitment-Charts-New-Territory, available at least as early as Feb. 14, 2017.
Official Publication of the Association of American Feed Control Officials (AAFCO), 2016. Available at www.aafco.org/Publications. (Reference Not Available).
Oosterom, Epidemiological studies and proposed preventive measures in the fight against human salmonellosis. Int J Food Microbiol 12, 41-51 (1991).
Pastagia et al., Lysins: the arrival of pathogen-directed anti-infectives. J Med Microbiol 62, 1506-1516 (2013).
Pei et al., PROMALS3D: a tool for multiple protein sequence and structure alignments. Nucleic Acids Res 36, 2295-2300 (2008).
Piddock, Does the use of antimicrobial agents in veterinary medicine and animal husbandry select antibiotic-resistant bacteria that infect man and compromise antimicrobial chemotherapy? J Antimicrob Chemother 38, 1-3 (1996).
USDA, Foreign Agricultural Service, "Livestock and Poultry: World Markets and Trade" Report available online at https://www.fas.usda.gov/data/livestock-and-poultry-world-markets-and-trade. Oct. 2016.
Ritter et al., "Engineering Antimicrobial Proteins and Probiotic Secretion Systems" Poster presented at the Science and Careers in Biotechnology Symposium, Sep. 9, 2016; 1 page.
Ruiz-Palacios et al., Experimental Campylobacter diarrhea in chickens. Infect Immun 34, 250-255 (1981).
Safety from farm to fork. Nat Rev Microbiol 7, 478 (2009).
Sambrook et al., 1989. Molecular cloning: a laboratory manual, 2nd ed. Cold Spring Harbor Laboratory Press, Cold Spring Harbor, N.Y.
Savva et al., Molecular architecture and functional analysis of NetB, a pore-forming toxin from Clostridium perfringens. J Biol Chem 288, 3512-3522 (2013).
Scallan et al., Foodborne illness acquired in the United States—major pathogens. Emerg Infect Dis 17, 7-15 (2011).
Scanlon et al., A high-throughput screen for antibiotic drug discovery. Biotechnol Bioeng 111, 232-243 (2014).
Schmitz et al., Lytic enzyme discovery through multigenomic sequence analysis in Clostridium perfringens. Appl Microbiol Biotechnol 89, 1783-1795 (2011).
Smith, Experiences with drug-free broiler production. Poult Sci 90, 2670-2678 (2011).
Stanfield et al., Campylobacter diarrhea in an adult mouse model. Microb Pathog 3, 155-165 (1987).
Statistical Yearbook of the Food And Agricultural Organization, available online at www.fao.org/docrep/018/i3107e/3107e.PDF, available at least as early as Feb. 14, 2017. (Reference Not Available).
Tatusova et al., BLAST 2 Sequences, a new tool for comparing protein and nucleotide sequences. FEMS Microbiol Lett 174, 247-250 (1999).
The Library of Congress THOMAS online collection https://www.congress.gov/bill/112th-congress/house-bill/965 Available at least as early as Feb. 14, 2017.
Tisakova et al., Bacteriophage endolysins and their use in biotechnological processes, The Journal of Microbiology, Biotechnology and Food Sciences, 3(2):164-170 (2014).
Toymentseva et al., The LIKE system, a novel protein expression toolbox for Bacillus subtilis based on the lial promoter. Microb Cell Fact 11, 143 (2012).
UniProtKB Accession No. B1R4A5 "Lysozyme" May 20, 2008 [oneline], www.uniprot.org/uniprot/B1R4A5.
US Poultry and Egg Association Economic Data, Available online at uspoultry.org/economic_data/, available at least as early as Feb. 14, 2017. (Reference Not Available).
Van Asseldonk et al., Cloning of usp45, a gene encoding a secreted protein from *Lactococcus lactis* subsp. lactis MG1363. Gene 95, 155-160 (1990).
Van Den Bogaard, Antimicrobial resistance—relation to human and animal exposure to antibiotics. J Antimicrob Chemother 40, 453-454 (1997).
Veterinary Feed Directive (VFD) final rule by FDA, (Jun. 3, 2015), Available at https://www.federalregister.gov/articles/2015/06/03/2015-13393/veterinary-feed-directive, available at least as early as Sep. 12, 2015.
Volzing et al., Antimicrobial peptides targeting Gram-negative pathogens, produced and delivered by lactic acid bacteria. ACS Synth Biol 2, 643-650 (2013).
Volzing et al., proTeOn and proTeOff, new protein devices that inducibly activate bacterial gene expression. ACS Chem Biol 6, 1107-1116 (2011).
Witte, Medical consequences of antibiotic use in agriculture. Science 279, 996-997 (1998).
Wu, The Potts model, Rev. Mod. Phys., 54, 235 (1982).
Zhang et al., Effect of a radiant energy-treated lysozyme antimicrobial blend on the control of clostridial necrotic enteritis in broiler chickens. Avian Dis 54, 1298-1300 (2010).
Zuidhof et al., Growth, efficiency, and yield of commercial broilers from 1957, 1978, and 2005. Poult Sci 93, 2970-2982 (2014).
FDA, #213, Guidance for Industry, New Animal Drugs and New Animal Drug Combination Products Administered in or on Medicated Feed or Drinking Water of Food-Producing Animals: Recommendations for Drug Sponsors for Voluntarily Aligning Product Use Conditions with GFI #209, Dec. 2013, available online at https://www.fda.gov/media/83488/download [last accessed Apr. 15, 2021].
FDA, Biannual Progress Report on Judicious Use of Antimicrobials in Food-producing Animals, Jan. 20, 2016, available online at https://wayback.archive-it.org/7993/20190208023235/https://www.fda.gov/AnimalVeterinary/NewsEvents/CVMUpdates/ucm482110.htm [last accessed Apr. 15, 2021].

* cited by examiner

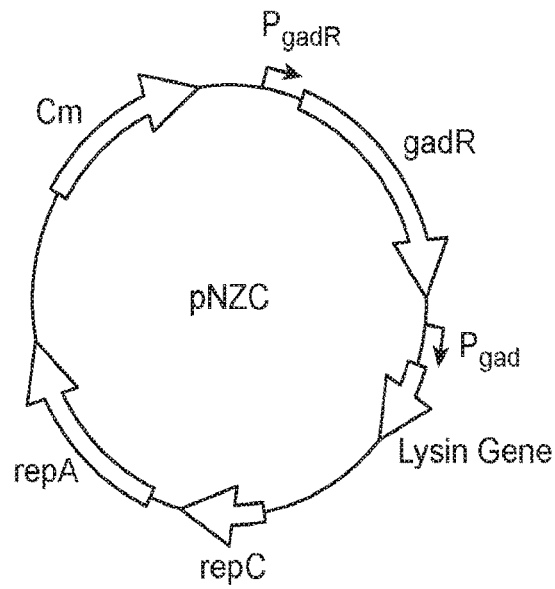

FIG. 2A

FIG. 2B

SEQ ID NO:1

```
MQSRSDSNFK GIDISNWQKG INLNQLKERG YDVCYIKITE GKGYVDPCFE ENYNKAIAAG    60
MKVGVYHYWR GTSSAIEQAN NIVRTLGNKH IDCKIAIDVE QTDGLSYGEL NNSVLQLAEE   120
LERLIGAEVC IYCNTNYARN VLDSRLGKYS LWVAHYGVNK PGDNPIWDKW AGFQYSENGT   180
SNVNGSLDLD EFTEEIFINK ESSKVTENKL FSTNARALVA LDPRDNPSDN YNDLGEIYEG   240
ERIQVLAEVC DKEDYLPVKY WKDSEGRESG KVWIRSKQDY MMIDTYHRVF NVITQLDARY   300
EPSSDSATMG YVKNGERLYV HRTEGNYSLC TYFAGNGYKT AWFTAKYLER I
```

FIG. 2C

SEQ ID NO:2

```
MNIKTDLTSV NYRNGRNGNS IDYIVCHFTG NQNDKASGNA NYFRCVNRQA SAHYFVDDNE    60
IVQVVREGDT SWHCGDGNGR YGITNSNSIG IEMCATNGDI SEKTIENTLW LVKSLMNKYG   120
IDIDHVVRHY DASRKCCPSP FSPNNWSRWW EFKERLKGTV ENIEVTTQST NGFYESDIEK   180
TNATIVGLGD IEVLNDKCEV IKDRYISSLD RIYVLGIYPS RNFIEVIYQG KDKKYHAYID   240
IKYYSRISFD FHMQYQNDDG DTYVWWSSKD VNKTEPNEIL SPNKKASPMY RENGWLRITF   300
YRDNGVATDG FVRYEGEQSV KFYEEGKIKD GIVKVNTYLN VRDSICGNII GKVFNGEEVS   360
IIWTKDGWYY IEYNTNHGKK RGYVSSKYVE EV
```

FIG. 2D

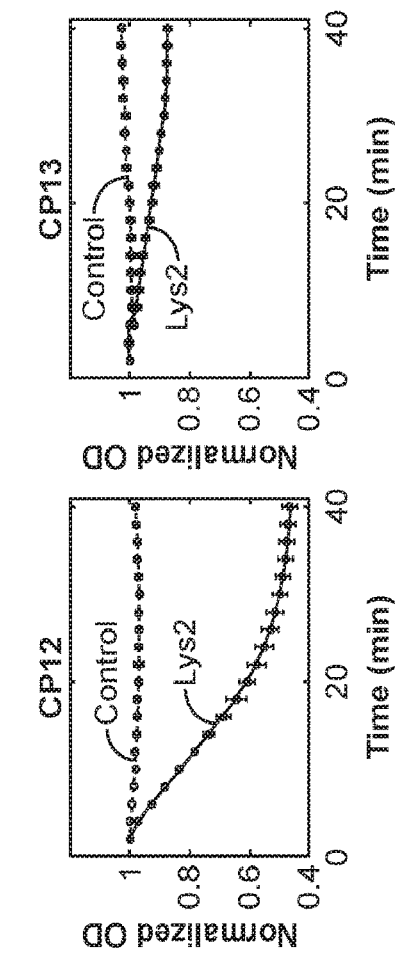
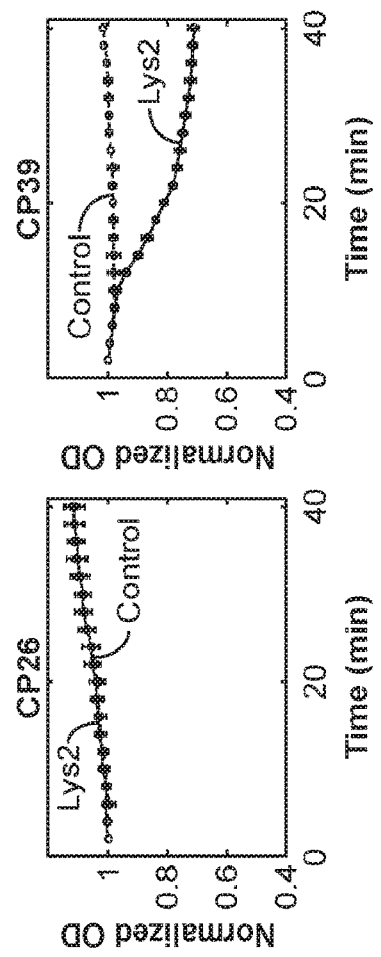
FIG. 3C
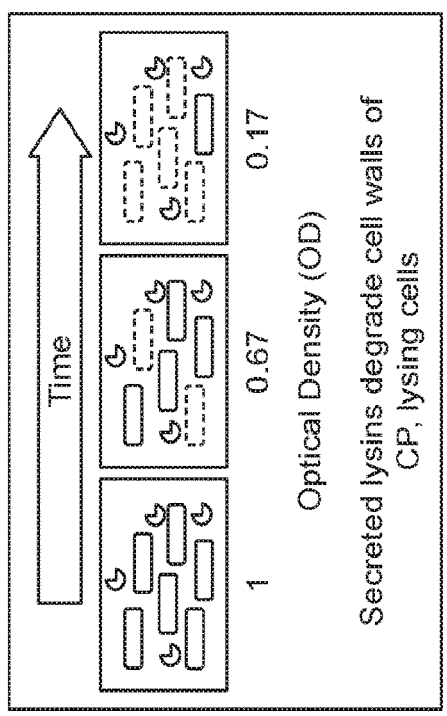
FIG. 3A
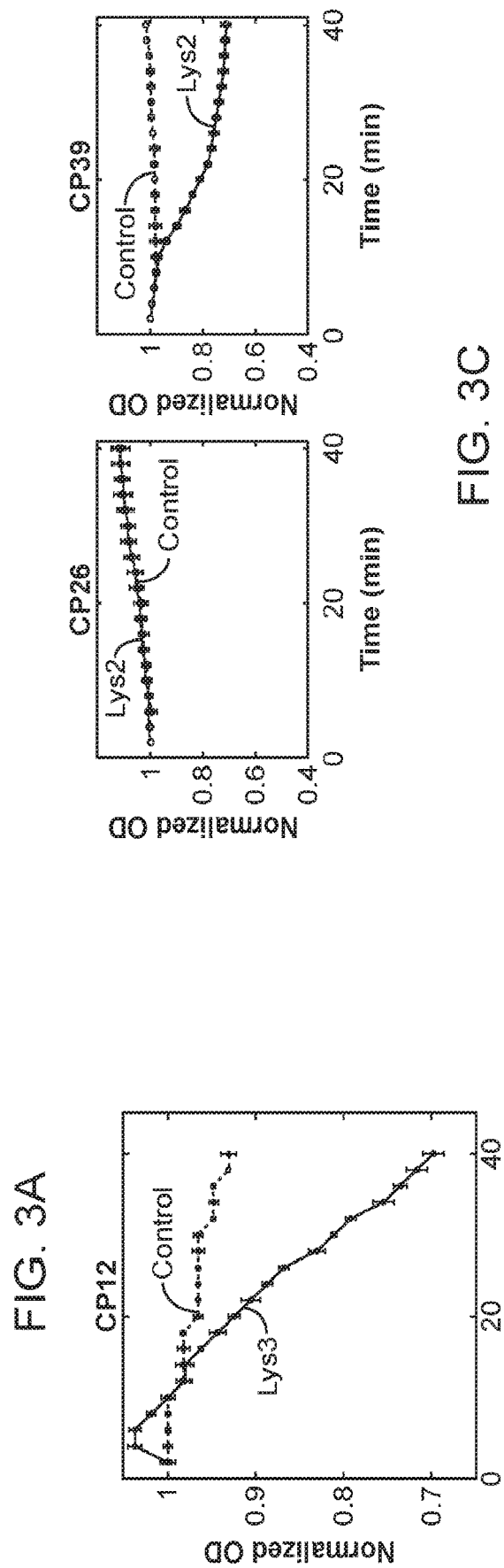
FIG. 3B

```
Lys2_Cat       MQSRSDSNFKGIDISNWQKGINLNQLKERGYDVCYIKITEGKGYVDPCFEENYNKAIAAG
Lys2Con_Cat    MEGRNNNNLKGIDVSNWQGNINFKSVKNDGIEVVYIKATEGDYFKDSYAKQNYERAKAEG
Lys2Con20_Cat  MQSRNNNNLKGIDVSNWQGNINFKSVKNDGIEVVYIKATEGDYFKDSYAKQNYEGAKANG
               *:. :*****:****:**:***:** ..:: *:.* ***:* **.:**:.**.  :* *

Lys2_Cat       MKVGVYHYWRGTSSAIEQANNIV---RTLGNKHIDCKIAIDVEQTDGLSYGELNNSVLQL
Lys2Con_Cat    LKVGFYHFFRPNKAKDQANYFIDYLNEIGATDYDCKLALDIETTEGRGAVDLTTMCIEF
Lys2Con20_Cat  LKVGFYHFFRPNKAKEQANYFISYLNGIGAKDYDCKLALDIETTEGLGAYELTTMCIEF
               :***.**::*.....:.** :.  ..  ...*...**:*::*:: :*  .  :. :::

Lys2_Cat       AEELERLIGAEVCIYCNTNYARNVLDSRLGKYSLWVAHYGVNKPGDNPIWDKWAGFQYSE
Lys2Con_Cat    LEEVRRITNREVVVYTYTSFANNNLDNRLGVYPLWIAHYGVKAPKDNNIWSSWIGFQYSD
Lys2Con20_Cat  LEEVKRLTGKEVVVYTYTSFANNNLDSRLGVYPLWIAHYGVKTPKDNNIWSSWIGFQYSD
                **::*:: .**. * :*.:** **.***.* **:****. .*.**.**..*.****:

Lys2_Cat       NGT-SNVNGSLDLDEFTEEIF-
Lys2Con_Cat    KGNVAGVSGNCDMNEFKEEIFD
Lys2Con20_Cat  KGSVAGVSGNCDMNEFTEEILI
               :*. :.*.*. *:::**.***:
```

FIG. 6

```
Lys2_CWBD  ------------------------------INK------------ESSKV
Lys3_CWBD  FSPNNWSRWWEFNERLNGTVENIEVTTQSTNGFYESDIEKTNATIVGLGDIEVLNDKCEV
                                         :**

Lys2_CWBD  TENKLFSTNAAR-ALVALDPRDNPSDNYNDLGRIYEGERIQVL---------
Lys3_CWBD  IKDRYTSSLDRIYVLGIY-----PSRNF---IEVIYQGRDKKYHAYIDIKYYSRTSFDFHMQ
            :.: :*..:: * *..     **.*:    **:*:.* .

Lys2_CWBD  ------------------------------AEVCDKEDYLPVKYWKDSEGRESGKVWI
Lys3_CWBD  YQNDDGDTYVSWSSKDVNKTEPNEILSPNKKASPMYRENGWLRITFYRDNGVATDGFVRY
                                         :: .:.:*:.:  .    .   *

Lys2_CWBD  RSKQDYMMIDT---YHRVENVITQLDARYEPSSDSATMGYVKNGERLYVHRTEGNYSLCT
Lys3_CWBD  EGEQSVKFYEEGNIKDGIVKVNTYLNV---RDSICGNIIGKVFNGEEVSIIWTKDGWYIE
            .:*. ::  :    : *:::.*. .    .**  .:  .*::*:.: : :. * * *

Lys2_CWBD  YFAGNGYKTAWFTAKYLERI
Lys3_CWBD  YNTNHGKKRGYVSSKYVEEV
           *  ..* *...*:*:*:.:
```

FIG. 7

```
Lys2_Cat       ------------------------------------------------MQSRSDSNFKGIDISNWQKGINLNQLKERGYDVCYIKITEGKGYVDPC
Lys2Con_Cat    ------------------------------------------------MEGRNNNNLKGIDVSNWQGNINFKSVKNDGIEVVYIKATEGDYFKDSY
Lys2Con20_Cat  ------------------------------------------------MQSPNNNNLKGIDVSNWQGNINFKSVKNDGIEVVYIKATEGDYFKDSY
                                                               :  *.  ..:..*:.**:.:: . ...::*.. :.**.:* *.

Lys3_Cat       ------------------------------------------NEIVQV-VREGDTSWHCG-------DGN
Lys2_Cat       FEENYNKAIAAGMKVGVYHYWRGTSSAIEQANNIV----RTLGNKHIDCKIAIDVEQTDGL
Lys2Con_Cat    AKQNYERAKAEGLKVGFYHFFRPNKNARDQANYFIDYLNEIGATDYDCKLALDIETTEGR
Lys2Con20_Cat  AKQNYEGAKANGLKVGFYHFFRPNKNAKEQANYFISYLNGIGAKDYDCKLALDIETTEGL
                 . *  . *  ::** *:   :   :.**  .            * .. *. :    *:

Lys3_Cat       GRYGITNSN--------SIGIEMCATN-GDISEKTIENTLWLVKSLMNKYGIDIDHVVR
Lys2_Cat       SYGELNNSVLQLAEELERLIGAEVCIYCNTNYARNVLDSRLGKYSLWVAHYGVNKPGDNP
Lys2Con_Cat    GAYDLTTMCIEFLEEVRRITNREVVYTSFANNNLDNRLGVYPLWIAHYGVKAPKDNN
Lys2Con20_Cat  GAYELTTMCIEFLEEVKRLTGKEVVYTYTSFANNNLDSRLGVYPLWIAHYGVKTFKDNN
                 *.: ..   :     .: .. * :    :  .:.:* *:: : *:.: .  .:*:;

Lys3_Cat       HYDA--------SRKC-------CPSP-------
Lys2_Cat       IWDKWAGFQYSENGT-SNVNGSLDLDEFTEEIF-
Lys2Con_Cat    IWSSWIGFQYSDKGNVAGVSGNCDMNEFKEEIFD
Lys2Con20_Cat  IWSSWIGFQYSDKGSVAGVSGNCDMNEFTEEILI
                 :                                
```

FIG. 8

SEQUENCE LISTING

<160> NUMBER OF SEQ ID NOS: 10

<210> SEQ ID NO 1
<211> LENGTH: 351
<212> TYPE: PRT
<213> ORGANISM: Clostridium perfringens

<400> SEQUENCE: 1

```
Met Gln Ser Arg Ser Asp Ser Asn Phe Lys Gly Ile Asp Ile Ser Asn
1               5                   10                  15

Trp Gln Lys Gly Ile Asn Leu Asn Gln Leu Lys Glu Arg Gly Tyr Asp
            20                  25                  30

Val Cys Tyr Ile Lys Ile Thr Glu Gly Lys Gly Tyr Val Asp Pro Cys
        35                  40                  45

Phe Glu Glu Asn Tyr Asn Lys Ala Ile Ala Gly Met Lys Val Gly
    50                  55                  60

Val Tyr His Tyr Trp Arg Gly Thr Ser Ser Ala Ile Glu Gln Ala Asn
65                  70                  75                  80

Asn Ile Val Arg Thr Leu Gly Asn Lys His Ile Asp Cys Lys Ile Ala
                85                  90                  95

Ile Asp Val Glu Gln Thr Asp Gly Leu Ser Tyr Gly Glu Leu Asn Asn
            100                 105                 110

Ser Val Leu Gln Leu Ala Glu Glu Leu Glu Arg Leu Ile Gly Ala Glu
        115                 120                 125

Val Cys Ile Tyr Cys Asn Thr Asn Tyr Ala Arg Asn Val Leu Asp Ser
130                 135                 140

Arg Leu Gly Lys Tyr Ser Leu Trp Val Ala His Tyr Gly Val Asn Lys
145                 150                 155                 160

Pro Gly Asp Asn Pro Ile Trp Asp Lys Trp Ala Gly Phe Gln Tyr Ser
                165                 170                 175

Glu Asn Gly Thr Ser Asn Val Asn Gly Ser Leu Asp Leu Asp Glu Phe
            180                 185                 190

Thr Glu Glu Ile Phe Ile Asn Lys Glu Ser Ser Lys Val Thr Glu Asn
        195                 200                 205

Lys Leu Phe Ser Thr Asn Ala Arg Ala Leu Val Ala Leu Asp Pro Arg
210                 215                 220

Asp Asn Pro Ser Asp Asn Tyr Asn Asp Leu Gly Glu Ile Tyr Glu Gly
225                 230                 235                 240

Glu Arg Ile Gln Val Leu Ala Glu Val Cys Asp Lys Glu Asp Tyr Leu
                245                 250                 255

Pro Val Lys Tyr Trp Lys Asp Ser Glu Gly Arg Glu Ser Gly Lys Val
            260                 265                 270

Trp Ile Arg Ser Lys Gln Asp Tyr Met Met Ile Asp Thr Tyr His Arg
        275                 280                 285

Val Phe Asn Val Ile Thr Gln Leu Asp Ala Arg Tyr Glu Pro Ser Ser
290                 295                 300

Asp Ser Ala Thr Met Gly Tyr Val Lys Asn Gly Glu Arg Leu Tyr Val
305                 310                 315                 320

His Arg Thr Glu Gly Asn Tyr Ser Leu Cys Thr Tyr Phe Ala Gly Asn
                325                 330                 335

Gly Tyr Lys Thr Ala Trp Phe Thr Ala Lys Tyr Leu Glu Arg Ile
            340                 345                 350
```

<210> SEQ ID NO 2
<211> LENGTH: 392
<212> TYPE: PRT
<213> ORGANISM: Clostridium perfringens

<400> SEQUENCE: 2

```
Met Asn Ile Lys Thr Asp Leu Thr Ser Val Asn Tyr Arg Asn Gly Arg
1               5                   10                  15
```

Asn Gly Asn Ser Ile Asp Tyr Ile Val Cys His Phe Thr Gly Asn Gln
            20                  25                  30

Asn Asp Lys Ala Ser Gly Asn Ala Asn Tyr Phe Arg Cys Val Asn Arg
            35                  40                  45

Gln Ala Ser Ala His Tyr Phe Val Asp Asp Asn Glu Ile Val Gln Val
    50                  55                  60

Val Arg Glu Gly Asp Thr Ser Trp His Cys Gly Asp Gly Asn Gly Arg
65                  70                  75                  80

Tyr Gly Ile Thr Asn Ser Asn Ser Ile Gly Ile Glu Met Cys Ala Thr
                85                  90                  95

Asn Gly Asp Ile Ser Glu Lys Thr Ile Glu Asn Thr Leu Trp Leu Val
            100                 105                 110

Lys Ser Leu Met Asn Lys Tyr Gly Ile Asp Ile Asp His Val Val Arg
            115                 120                 125

His Tyr Asp Ala Ser Arg Lys Cys Cys Pro Ser Pro Phe Ser Pro Asn
    130                 135                 140

Asn Trp Ser Arg Trp Glu Phe Lys Glu Arg Leu Lys Gly Thr Val
145                 150                 155                 160

Glu Asn Ile Glu Val Thr Thr Gln Ser Thr Asn Gly Phe Tyr Glu Ser
                165                 170                 175

Asp Ile Glu Lys Thr Asn Ala Thr Ile Val Gly Leu Gly Asp Ile Glu
            180                 185                 190

Val Leu Asn Asp Lys Cys Glu Val Ile Lys Asp Arg Tyr Ile Ser Ser
            195                 200                 205

Leu Asp Arg Ile Tyr Val Leu Gly Ile Tyr Pro Ser Arg Asn Phe Ile
    210                 215                 220

Glu Val Ile Tyr Gln Gly Lys Asp Lys Lys Tyr His Ala Tyr Ile Asp
225                 230                 235                 240

Ile Lys Tyr Tyr Ser Arg Ile Ser Phe Asp Phe His Met Gln Tyr Gln
                245                 250                 255

Asn Asp Asp Gly Asp Thr Tyr Val Trp Trp Ser Ser Lys Asp Val Asn
            260                 265                 270

Lys Thr Glu Pro Asn Glu Ile Leu Ser Pro Asn Lys Lys Ala Ser Pro
            275                 280                 285

Met Tyr Arg Glu Asn Gly Trp Leu Arg Ile Thr Phe Tyr Arg Asp Asn
    290                 295                 300

Gly Val Ala Thr Asp Gly Phe Val Arg Tyr Glu Gly Glu Gln Ser Val
305                 310                 315                 320

Lys Phe Tyr Glu Glu Gly Lys Ile Lys Asp Gly Ile Val Lys Val Asn
                325                 330                 335

Thr Tyr Leu Asn Val Arg Asp Ser Ile Cys Gly Asn Ile Ile Gly Lys
            340                 345                 350

Val Phe Asn Gly Glu Glu Val Ser Ile Ile Trp Thr Lys Asp Gly Trp
            355                 360                 365

Tyr Tyr Ile Glu Tyr Asn Thr Asn His Gly Lys Lys Arg Gly Tyr Val
    370                 375                 380

Ser Ser Lys Tyr Val Glu Glu Val
385                 390

<210> SEQ ID NO 3
<211> LENGTH: 202
<212> TYPE: PRT
<213> ORGANISM: artificial
<220> FEATURE:

<223> OTHER INFORMATION: Engineered lysin catalytic domain

<400> SEQUENCE: 3

Met Glu Gly Arg Asn Asn Asn Leu Lys Gly Ile Asp Val Ser Asn
1               5                   10                  15

Trp Gln Gly Asn Ile Asn Phe Lys Ser Val Lys Asn Asp Gly Ile Glu
            20                  25                  30

Val Val Tyr Ile Lys Ala Thr Glu Gly Asp Tyr Phe Lys Asp Ser Tyr
        35                  40                  45

Ala Lys Gln Asn Tyr Glu Arg Ala Lys Ala Glu Gly Leu Lys Val Gly
    50                  55                  60

Phe Tyr His Phe Arg Pro Asn Lys Asn Ala Lys Asp Gln Ala Asn
65              70                  75                  80

Tyr Phe Ile Asp Tyr Leu Asn Glu Ile Gly Ala Thr Asp Tyr Asp Cys
                85                  90                  95

Lys Leu Ala Leu Asp Ile Glu Thr Thr Glu Gly Arg Gly Ala Tyr Asp
            100                 105                 110

Leu Thr Thr Met Cys Ile Glu Phe Leu Glu Glu Val Arg Arg Ile Thr
            115                 120                 125

Asn Arg Glu Val Val Tyr Thr Tyr Thr Ser Phe Ala Asn Asn Asn
130                 135                 140

Leu Asp Asn Arg Leu Gly Val Tyr Pro Leu Trp Ile Ala His Tyr Gly
145                 150                 155                 160

Val Lys Ala Pro Lys Asp Asn Asn Ile Trp Ser Ser Trp Ile Gly Phe
                165                 170                 175

Gln Tyr Ser Asp Lys Gly Asn Val Ala Gly Val Ser Gly Asn Cys Asp
            180                 185                 190

Met Asn Glu Phe Lys Glu Glu Ile Phe Asp
            195                 200

<210> SEQ ID NO 4
<211> LENGTH: 202
<212> TYPE: PRT
<213> ORGANISM: artificial
<220> FEATURE:
<223> OTHER INFORMATION: Engineered lysin catalytic domain

<400> SEQUENCE: 4

Met Gln Ser Arg Asn Asn Asn Leu Lys Gly Ile Asp Val Ser Asn
1               5                   10                  15

Trp Gln Gly Asn Ile Asn Phe Lys Ser Val Lys Asn Asp Gly Ile Glu
            20                  25                  30

Val Val Tyr Ile Lys Ala Thr Glu Gly Asp Tyr Phe Lys Asp Ser Tyr
        35                  40                  45

Ala Lys Gln Asn Tyr Glu Gly Ala Lys Ala Asn Gly Leu Lys Val Gly
    50                  55                  60

Phe Tyr His Phe Arg Pro Asn Lys Asn Ala Lys Glu Gln Ala Asn
65              70                  75                  80

Tyr Phe Ile Ser Tyr Leu Asn Gly Ile Gly Ala Lys Asp Tyr Asp Cys
                85                  90                  95

Lys Leu Ala Leu Asp Ile Glu Thr Thr Glu Gly Leu Gly Ala Tyr Glu
            100                 105                 110

Leu Thr Thr Met Cys Ile Glu Phe Leu Glu Glu Val Lys Arg Leu Thr
            115                 120                 125

Gly Lys Glu Val Val Val Tyr Thr Tyr Thr Ser Phe Ala Asn Asn Asn
130                 135                 140

Leu Asp Ser Arg Leu Gly Val Tyr Pro Leu Trp Ile Ala His Tyr Gly
145                 150                 155                 160

Val Lys Thr Pro Lys Asp Asn Asn Ile Trp Ser Ser Trp Ile Gly Phe
            165                 170                 175

Gln Tyr Ser Asp Lys Gly Ser Val Ala Gly Val Ser Gly Asn Cys Asp
            180                 185                 190

Met Asn Glu Phe Thr Glu Glu Ile Leu Ile
        195                 200

<210> SEQ ID NO 5
<211> LENGTH: 356
<212> TYPE: PRT
<213> ORGANISM: artificial
<220> FEATURE:
<223> OTHER INFORMATION: Engineered lysin

<400> SEQUENCE: 5

Met Glu Gly Arg Asn Asn Asn Leu Lys Gly Ile Asp Val Ser Asn
1               5                   10                  15

Trp Gln Gly Asn Ile Asn Phe Lys Ser Val Lys Asn Asp Gly Ile Glu
            20                  25                  30

Val Val Tyr Ile Lys Ala Thr Glu Gly Asp Tyr Phe Lys Asp Ser Tyr
            35                  40                  45

Ala Lys Gln Asn Tyr Glu Arg Ala Lys Ala Glu Gly Leu Lys Val Gly
        50                  55                  60

Phe Tyr His Phe Phe Arg Pro Asn Lys Asn Ala Lys Asp Gln Ala Asn
65                  70                  75                  80

Tyr Phe Ile Asp Tyr Leu Asn Glu Ile Gly Ala Thr Asp Tyr Asp Cys
                85                  90                  95

Lys Leu Ala Leu Asp Ile Glu Thr Thr Glu Gly Arg Gly Ala Tyr Asp
            100                 105                 110

Leu Thr Thr Met Cys Ile Glu Phe Leu Glu Glu Val Arg Arg Ile Thr
            115                 120                 125

Asn Arg Glu Val Val Val Tyr Thr Tyr Thr Ser Phe Ala Asn Asn Asn
130                 135                 140

Leu Asp Asn Arg Leu Gly Val Tyr Pro Leu Trp Ile Ala His Tyr Gly
145                 150                 155                 160

Val Lys Ala Pro Lys Asp Asn Asn Ile Trp Ser Ser Trp Ile Gly Phe
            165                 170                 175

Gln Tyr Ser Asp Lys Gly Asn Val Ala Gly Val Ser Gly Asn Cys Asp
            180                 185                 190

Met Asn Glu Phe Lys Glu Glu Ile Phe Asp Ile Asn Lys Glu Ser Ser
        195                 200                 205

Lys Val Thr Glu Asn Lys Leu Phe Ser Thr Asn Ala Arg Ala Leu Val
        210                 215                 220

Ala Leu Asp Pro Arg Asp Asn Pro Ser Asp Tyr Asn Asp Leu Gly
225                 230                 235                 240

Glu Ile Tyr Glu Gly Glu Arg Ile Gln Val Leu Ala Glu Val Cys Asp
            245                 250                 255

Lys Glu Asp Tyr Leu Pro Val Lys Tyr Trp Lys Asp Ser Glu Gly Arg
            260                 265                 270

Glu Ser Gly Lys Val Trp Ile Arg Ser Lys Gln Asp Tyr Met Met Ile
        275                 280                 285

Asp Thr Tyr His Arg Val Phe Asn Val Ile Thr Gln Leu Asp Ala Arg
290                 295                 300

```
Tyr Glu Pro Ser Ser Asp Ser Ala Thr Met Gly Tyr Val Lys Asn Gly
305                 310                 315                 320

Glu Arg Leu Tyr Val His Arg Thr Glu Gly Asn Tyr Ser Leu Cys Thr
            325                 330                 335

Tyr Phe Ala Gly Asn Gly Tyr Lys Thr Ala Trp Phe Thr Ala Lys Tyr
        340                 345                 350

Leu Glu Arg Ile
        355

<210> SEQ ID NO 6
<211> LENGTH: 356
<212> TYPE: PRT
<213> ORGANISM: artificial
<220> FEATURE:
<223> OTHER INFORMATION: Engineered lysin

<400> SEQUENCE: 6

Met Gln Ser Arg Asn Asn Asn Leu Lys Gly Ile Asp Val Ser Asn
1               5                   10                  15

Trp Gln Gly Asn Ile Asn Phe Lys Ser Val Lys Asn Asp Gly Ile Glu
            20                  25                  30

Val Val Tyr Ile Lys Ala Thr Glu Gly Asp Tyr Phe Lys Asp Ser Tyr
            35                  40                  45

Ala Lys Gln Asn Tyr Glu Gly Ala Lys Ala Asn Gly Leu Lys Val Gly
        50                  55                  60

Phe Tyr His Phe Phe Arg Pro Asn Lys Asn Ala Lys Glu Gln Ala Asn
65                  70                  75                  80

Tyr Phe Ile Ser Tyr Leu Asn Gly Ile Gly Ala Lys Asp Tyr Asp Cys
                85                  90                  95

Lys Leu Ala Leu Asp Ile Glu Thr Glu Gly Leu Gly Ala Tyr Glu
            100                 105                 110

Leu Thr Thr Met Cys Ile Glu Phe Leu Glu Glu Val Lys Arg Leu Thr
            115                 120                 125

Gly Lys Glu Val Val Val Tyr Thr Tyr Thr Ser Phe Ala Asn Asn Asn
130                 135                 140

Leu Asp Ser Arg Leu Gly Val Tyr Pro Leu Trp Ile Ala His Tyr Gly
145                 150                 155                 160

Val Lys Thr Pro Lys Asp Asn Asn Ile Trp Ser Ser Trp Ile Gly Phe
                165                 170                 175

Gln Tyr Ser Asp Lys Gly Ser Val Ala Gly Val Ser Gly Asn Cys Asp
            180                 185                 190

Met Asn Glu Phe Thr Glu Glu Ile Leu Ile Asn Lys Glu Ser Ser
            195                 200                 205

Lys Val Thr Glu Asn Lys Leu Phe Ser Thr Asn Ala Arg Ala Leu Val
210                 215                 220

Ala Leu Asp Pro Arg Asp Asn Pro Ser Asp Asn Tyr Asn Asp Leu Gly
225                 230                 235                 240

Glu Ile Tyr Glu Gly Glu Arg Ile Gln Val Leu Ala Glu Val Cys Asp
                245                 250                 255

Lys Glu Asp Tyr Leu Pro Val Lys Tyr Trp Lys Asp Ser Glu Gly Arg
            260                 265                 270

Glu Ser Gly Lys Val Trp Ile Arg Ser Lys Gln Asp Tyr Met Met Ile
        275                 280                 285

Asp Thr Tyr His Arg Val Phe Asn Val Ile Thr Gln Leu Asp Ala Arg
290                 295                 300
```

Tyr Glu Pro Ser Ser Asp Ser Ala Thr Met Gly Tyr Val Lys Asn Gly
305                 310                 315                 320

Glu Arg Leu Tyr Val His Arg Thr Glu Gly Asn Tyr Ser Leu Cys Thr
            325                 330                 335

Tyr Phe Ala Gly Asn Gly Tyr Lys Thr Ala Trp Phe Thr Ala Lys Tyr
        340                 345                 350

Leu Glu Arg Ile
    355

<210> SEQ ID NO 7
<211> LENGTH: 197
<212> TYPE: PRT
<213> ORGANISM: Clostridium perfringens

<400> SEQUENCE: 7

Met Gln Ser Arg Ser Asp Ser Asn Phe Lys Gly Ile Asp Ile Ser Asn
1               5                   10                  15

Trp Gln Lys Gly Ile Asn Leu Asn Gln Leu Lys Glu Arg Gly Tyr Asp
            20                  25                  30

Val Cys Tyr Ile Lys Ile Thr Glu Gly Lys Gly Tyr Val Asp Pro Cys
        35                  40                  45

Phe Glu Glu Asn Tyr Asn Lys Ala Ile Ala Ala Gly Met Lys Val Gly
    50                  55                  60

Val Tyr His Tyr Trp Arg Gly Thr Ser Ser Ala Ile Glu Gln Ala Asn
65                  70                  75                  80

Asn Ile Val Arg Thr Leu Gly Asn Lys His Ile Asp Cys Lys Ile Ala
                85                  90                  95

Ile Asp Val Glu Gln Thr Asp Gly Leu Ser Tyr Gly Glu Leu Asn Asn
            100                 105                 110

Ser Val Leu Gln Leu Ala Glu Glu Leu Glu Arg Leu Ile Gly Ala Glu
        115                 120                 125

Val Cys Ile Tyr Cys Asn Thr Asn Tyr Ala Arg Asn Val Leu Asp Ser
    130                 135                 140

Arg Leu Gly Lys Tyr Ser Leu Trp Val Ala His Tyr Gly Val Asn Lys
145                 150                 155                 160

Pro Gly Asp Asn Pro Ile Trp Asp Lys Trp Ala Gly Phe Gln Tyr Ser
                165                 170                 175

Glu Asn Gly Thr Ser Asn Val Asn Gly Ser Leu Asp Leu Asp Glu Phe
            180                 185                 190

Thr Glu Glu Ile Phe
        195

<210> SEQ ID NO 8
<211> LENGTH: 140
<212> TYPE: PRT
<213> ORGANISM: Clostridium perfringens

<400> SEQUENCE: 8

Met Asn Ile Lys Thr Asp Leu Thr Ser Val Asn Tyr Arg Asn Gly Arg
1               5                   10                  15

Asn Gly Asn Ser Ile Asp Tyr Ile Val Cys His Phe Thr Gly Asn Gln
            20                  25                  30

Asn Asp Lys Ala Ser Gly Asn Ala Asn Tyr Phe Arg Cys Val Asn Arg
        35                  40                  45

Gln Ala Ser Ala His Tyr Phe Val Asp Asp Asn Glu Ile Val Gln Val
    50                  55                  60

Val Arg Glu Gly Asp Thr Ser Trp His Cys Gly Asp Gly Asn Gly Arg
65                  70                  75                  80

Tyr Gly Ile Thr Asn Ser Asn Ser Ile Gly Ile Glu Met Cys Ala Thr
            85                  90                  95

Asn Gly Asp Ile Ser Glu Lys Thr Ile Glu Asn Thr Leu Trp Leu Val
            100                 105                 110

Lys Ser Leu Met Asn Lys Tyr Gly Ile Asp Ile Asp His Val Val Arg
            115                 120                 125

His Tyr Asp Ala Ser Arg Lys Cys Cys Pro Ser Pro
130                 135                 140

<210> SEQ ID NO 9
<211> LENGTH: 154
<212> TYPE: PRT
<213> ORGANISM: Clostridium perfringens

<400> SEQUENCE: 9

Ile Asn Lys Glu Ser Ser Lys Val Thr Glu Asn Lys Leu Phe Ser Thr
1               5                   10                  15

Asn Ala Arg Ala Leu Val Ala Leu Asp Pro Arg Asp Asn Pro Ser Asp
            20                  25                  30

Asn Tyr Asn Asp Leu Gly Glu Ile Tyr Glu Gly Glu Arg Ile Gln Val
            35                  40                  45

Leu Ala Glu Val Cys Asp Lys Glu Asp Tyr Leu Pro Val Lys Tyr Trp
50                  55                  60

Lys Asp Ser Glu Gly Arg Glu Ser Gly Lys Val Trp Ile Arg Ser Lys
65                  70                  75                  80

Gln Asp Tyr Met Met Ile Asp Thr Tyr His Arg Val Phe Asn Val Ile
            85                  90                  95

Thr Gln Leu Asp Ala Arg Tyr Glu Pro Ser Ser Asp Ser Ala Thr Met
            100                 105                 110

Gly Tyr Val Lys Asn Gly Glu Arg Leu Tyr Val His Arg Thr Glu Gly
            115                 120                 125

Asn Tyr Ser Leu Cys Thr Tyr Phe Ala Gly Asn Gly Tyr Lys Thr Ala
            130                 135                 140

Trp Phe Thr Ala Lys Tyr Leu Glu Arg Ile
145                 150

<210> SEQ ID NO 10
<211> LENGTH: 252
<212> TYPE: PRT
<213> ORGANISM: Clostridium perfringens

<400> SEQUENCE: 10

Phe Ser Pro Asn Asn Trp Ser Arg Trp Trp Glu Phe Lys Glu Arg Leu
1               5                   10                  15

Lys Gly Thr Val Glu Asn Ile Glu Val Thr Thr Gln Ser Thr Asn Gly
            20                  25                  30

Phe Tyr Glu Ser Asp Ile Glu Lys Thr Asn Ala Thr Ile Val Gly Leu
            35                  40                  45

Gly Asp Ile Glu Val Leu Asn Asp Lys Cys Glu Val Ile Lys Asp Arg
50                  55                  60

Tyr Ile Ser Ser Leu Asp Arg Ile Tyr Val Leu Gly Ile Tyr Pro Ser
65                  70                  75                  80

Arg Asn Phe Ile Glu Val Ile Tyr Gln Gly Lys Asp Lys Lys Tyr His
            85                  90                  95

-continued

```
Ala Tyr Ile Asp Ile Lys Tyr Tyr Ser Arg Ile Ser Phe Asp Phe His
            100                 105                 110

Met Gln Tyr Gln Asn Asp Asp Gly Asp Thr Tyr Val Trp Trp Ser Ser
        115                 120                 125

Lys Asp Val Asn Lys Thr Glu Pro Asn Glu Ile Leu Ser Pro Asn Lys
    130                 135                 140

Lys Ala Ser Pro Met Tyr Arg Glu Asn Gly Trp Leu Arg Ile Thr Phe
145                 150                 155                 160

Tyr Arg Asp Asn Gly Val Ala Thr Asp Gly Phe Val Arg Tyr Glu Gly
                165                 170                 175

Glu Gln Ser Val Lys Phe Tyr Glu Glu Gly Lys Ile Lys Asp Gly Ile
            180                 185                 190

Val Lys Val Asn Thr Tyr Leu Asn Val Arg Asp Ser Ile Cys Gly Asn
        195                 200                 205

Ile Ile Gly Lys Val Phe Asn Gly Glu Glu Val Ser Ile Ile Trp Thr
        210                 215                 220

Lys Asp Gly Trp Tyr Tyr Ile Glu Tyr Asn Thr Asn His Gly Lys Lys
225                 230                 235                 240

Arg Gly Tyr Val Ser Ser Lys Tyr Val Glu Glu Val
                245                 250
```

VECTORS, GENETICALLY MODIFIED BACTERIA, AND METHODS OF MAKING AND USING

CONTINUING APPLICATION DATA

This application is the § 371 U.S. National Stage of International Application No. PCT/US2018/049881, filed Sep. 7, 2018, which claims the benefit of U.S. Provisional Application Ser. No. 62/555,962, filed Sep. 8, 2017, the disclosures of each of which are incorporated by reference herein in their entireties.

GOVERNMENT FUNDING

This invention was made with government support under GM111358 awarded by the National Institutes of Health and CBET-1412283 awarded by the National Science Foundation. The government has certain rights in the invention.

SEQUENCE LISTING

This application contains a Sequence Listing electronically submitted to the United States Patent and Trademark Office via EFS-Web as an ASCII text file entitled "110-05670201 ST25.txt" having a size of 22 kilobytes and created on Aug. 24, 2018. Due to the electronic filing of the Sequence Listing, the electronically submitted Sequence Listing serves as both the paper copy required by 37 CFR § 1.821(c) and the CRF required by § 1.821(e).

BACKGROUND

Chicken is a part of diets globally. More than 116 million metric tons of poultry meat was consumed in 2016 worldwide (Report by the Foreign Agricultural Service of the USDA, available on the world wide web at fas.usda.gov/data/livestock-and-poultry-world-markets-and-trade; FAO Statistical Yearbook, available on the world wide web at fao.org/docrep/018/i3107e/i3107e.PDF). Demand for chicken has increased by an average 2.9% over the past 15 years, and demand is projected by the Food and Agriculture Organization of the United Nations to continue growing over the next decade.

In the US, production of broiler chickens topped 40 billion pounds in 2015. Per capita annual chicken consumption has doubled to over 90 pounds since 1980 (National Chicken Council Statistics, available on the world wide web at nationalchickencouncil.org/about-the-industry/statistics/per-capita-consumption-of-poultry-and-livestock-1965-to-estimated-2012-in-pounds/). There are now over 9 billion broilers produced in the US every year. In 2015, poultry sales in the US topped $28 billion (id.; US Poultry and Egg Association Economic Data, available on the world wide web at uspoultry.org/economic_data/). This vast demand has been met thanks to significant increases in productivity of the broiler chicken industry. From 1957 to 2005, broiler size increased by over 400% (Zuidhof et al., Poult Sci. 2014; 93(12):2970-82), with a concurrent 50 percent (%) reduction in the feed conversion ratio (weight of feed used per weight of bird gained) to a current average of 1.6. Feed accounts for up to 70% of cost. As a result, despite increasing demand, the price of poultry has risen at about half the rate of other consumer goods from 1960 to 2004 (id.).

This profound change in productivity has been achieved largely via intentional breed selection. Importantly, productivity has been largely sustained with the use of antibiotics. Antibiotics have been used for decades in livestock production with established benefits, keeping flocks healthy, promoting animal growth and improving feed efficiency (Piddock, J. Antimicrob. Chemother. 1996; 38:1-2; Van den Bogaard, J. Antimicrob. Chemother. 1997; 40:453-4. Editorial, Safety from farm to fork, Nat. Rev. Microbiology 2009; 7:478; Consumer Reports: Meat on Drugs: The overuse of antibiotics in food animals & what supermarkets and consumers can do to stop it, 2012, available on the world wide web at consumersunion.org/wp-content/uploads/2012/06/CR_Meat_On_Drugs_Report_06-12.pdf.)

Two major trends have emerged recently that are exerting pressure on chicken producers to withdraw antibiotics from production. First, consumers, particularly in developed countries, are resisting the presence of chemicals in their food. Regardless of the actual risk to the health of consumers, antibiotics are perceived as undesirable additives in meat. As a result, major chicken producers are branding their products as "Antibiotics Free" (Kesmodel, "Meat Companies Go Antibiotics-Free as More Consumers Demand It," Wall Street Journal, Nov. 3, 2014, available on the world wide web at wsj.com/articles/meat-companies-go-antibiotics-free-as-more-consumers-demand-it-1415071802). Wholesale chicken consumers, such as fast-food chains, are also marketing their products as free of antibiotics, in response to consumer demand. (White, Science, 1998; 279: 996).

Second, a major concern of public health officials is the continuing emergence of antimicrobial resistance to existing antibiotics (Mellon et al. Hogging it! Estimates of antimicrobial abuse in livestock. Union of Concerned Scientists, 2001, available on the world wide web at ucsusa.org/publications; Joint FAO/WHO/OIE Expert Meeting on Critically Important Antimicrobials, Rome, Italy, November 2007, available on the world wide web at who.int/foodborne_disease/resources/Report_CIA_Meeting.pdf; Khachatourians, CMAJ. 1998; 159:1129-36). Numerous cases have been reported of antibiotic-resistant food-borne pathogens, including *Salmonella* spp. (Melbak et al., N Engl. J. Med. 1999; 341:1420-1425; Glenn et al., Microb. Drug Resist. 2011; 17(3):407-18. Karon et al., Emerg. Infect. Dis. 2007; 13(11):1777-1780). One significant source of drug-resistance emergence globally is the widespread use of antibiotics in farm animal production (FDA, Guidance for Industry #209, The Judicious Use of Medically Important Antimicrobial Drugs in Food-Producing Animals; World Health Organization, Global action plan on antimicrobial resistance, 2015, ISBN: 9789241509763). In 2012, an estimated 70% of the total amount of antibiotics produced in the United States was administered to cattle, pigs, and poultry, to promote growth and improve feed efficiency, even in the absence of infection. This sub-therapeutic administration of antibiotics to animals creates a vast reservoir for the selection of drug-resistant bacteria that can infect humans through food.

The precise contribution of antibiotics used in livestock to human infections by antibiotic-resistant microbes is under contentious debate (see, e.g. Smith, Poult. Sci. 2011; 90(11): 2670-2678). In complex systems such as food production, it is difficult to establish causal relationships between the use of antibiotics in animal feed and infections where antibiotic-resistant microbes affect human populations. Nevertheless, there is undisputed evidence that transmission of resistant strains to humans can occur through food (Lungu et al. Foodborne Pathog. Dis. 2011; 8(5):569-78. Jacob et al. Foodborne Pathog. Dis. 2008; 5(6):721-30; Oosterom, Int. J. Food Microbiol. 1991; 12:41-51).

Because of these concerns, the European Union banned the use of antibiotics in food animal production in 2006 (Casewell et al., J. Antimicrobial Chemotherapy 2003; 52:159-161). Attempts have been made to pass similar measures in the United States with legislation introduced in Congress. The attempts to pass this law have been met with resistance. There are, indeed, many important and demonstrated benefits to using antibiotics in livestock production. Thus, a widespread ban on their use in the absence of alternative antibiotic technologies will likely result in increased food prices (McEwen et al. Clin. Infect. Dis 2002; 34:S93-S106). This ban may diminish the enormous positive impact of the US animal agriculture on the economy, estimated at over $100 billion annually. It could also jeopardize the global supply of abundant, high-quality, nutritious, safe and relatively inexpensive food.

Nevertheless, the FDA has moved to curtail the use of medically important antibiotics for livestock production purposes. Drug companies are voluntarily adopting FDA Guidance #209 and FDA Guidance #213, revising the FDA-approved labeled use conditions to remove the use of antimicrobial drugs for production purposes. According to the January 2016 FDA Biannual Progress Report on Judicious Use of Antimicrobials in Food-producing Animals, "All of the affected drug sponsors have committed in writing to making the changes described in the guidance by the end of 2016." Beginning on Jan. 1, 2017, over-the-counter antibiotics ceased being used in animal production. Antibiotics are now only prescribed by licensed veterinarians for sick animals.

Because of the effective ban on preventative use of antibiotics and because of the ease with which pathogens can spread in animals during mass production, a higher carriage of pathogens in live animals and, consequently, a significant impact on productivity because of less healthy flocks, may be observed. There may also be a higher frequency of contaminated food produced and delivered to consumers.

This confluence of events is adding to the need to develop and test new antimicrobial technologies to eliminate pathogens in animals, to reduce the use of antibiotics in agriculture, and to lower the risk of human disease caused by foodborne pathogens.

SUMMARY OF THE INVENTION

This disclosure describes compositions and methods that may be used to reduce the use of antibiotics in agriculture. For example, this disclosure describes certain antimicrobial peptides (AMPs), a vector encoding an AMP, a genetically modified bacterium including the vector, methods of making the bacterium, methods of using the bacterium, and kits including the bacterium. In some embodiments, the vector and/or the genetically engineered bacterium are preferably suitable for the treatment and/or control of a pathogenic microbe including, for example, *Clostridium perfringens* (CP).

In another aspect, this disclosure describes a lysin catalytic domain generative model and novel lysin catalytic domains and lysins generated, at least in part, using the lysin catalytic domain generative model. In some embodiments, a lysin—including a lysin generated in whole or in part using the lysin catalytic domain generative model—may be used to eliminate pathogens in animals.

In one aspect, this disclosure describes a vector that includes a coding region encoding a heterologous promoter operably linked to a coding region encoding an antimicrobial peptide. In some embodiments, the antimicrobial peptide includes a sequence having at least 80% homology to at least one of the catalytic domain of Lysin 2 (Lys2), the catalytic domain of Lysin 3 (Lys3), Lys2ConCat (SEQ ID NO:3), and Lys2Con20Cat (SEQ ID NO:4). In another aspect, this disclosure describes a kit that includes the vector.

In yet another aspect, this disclosure describes a genetically modified bacterium including the vector. In a further aspect, this disclosure describes a kit that includes the genetically modified bacterium. In an additional aspect, this disclosure describes a method that includes exposing a pathogenic microbe to the genetically modified bacterium.

In a further aspect, this disclosure describes a composition that includes a peptide, the peptide including a sequence having at least 80% homology to at least one of Lys2ConCat (SEQ ID NO:3) and Lys2Con20Cat (SEQ ID NO:4).

In an additional aspect, this disclosure describes a method that includes: aligning two or more lysin catalytic domain sequences to provide a multiple sequence alignment; and deriving a consensus sequence from the multiple sequence alignment may form a seed sequence.

In a further aspect, this disclosure describes a lysin catalytic domain sequence generated using the methods described herein. In an additional aspect, this disclosure describes a lysin that includes the lysin catalytic domain sequence generated using the methods described herein, a vector including that lysin, and a genetically modified bacterium including the vector.

As used herein, the term "protein" refers broadly to a polymer of two or more amino acids joined together by peptide bonds. The term "protein" also includes molecules which contain more than one protein joined by a disulfide bond, or complexes of proteins that are joined together, covalently or noncovalently, as multimers (for example, dimers, trimers, tetramers). Thus, the terms peptide, oligopeptide, enzyme, subunit, and protein are all included within the definition of protein and these terms are used interchangeably. It should be understood that these terms do not connote a specific length of a polymer of amino acids, nor are they intended to imply or distinguish whether the protein is produced using recombinant techniques, chemical or enzymatic synthesis, or is naturally occurring.

As used herein, the term "polynucleotide" refers to a polymeric form of nucleotides of any length, either ribonucleotides or deoxynucleotides, and includes both double- and single-stranded RNA and DNA. A polynucleotide can be obtained directly from a natural source, or can be prepared with the aid of recombinant, enzymatic, or chemical techniques. A polynucleotide can be linear or circular in topology. A polynucleotide may be, for example, a portion of a vector, such as an expression or cloning vector, or a fragment. A polynucleotide may include nucleotide sequences having different functions, including, for instance, coding regions, and non-coding regions such as regulatory regions.

As used herein, the terms "coding region," "coding sequence," and "open reading frame" are used interchangeably and refer to a nucleotide sequence that encodes a protein and, when placed under the control of appropriate regulatory sequences expresses the encoded protein. The boundaries of a coding region are generally determined by a translation start codon at its 5' end and a translation stop codon at its 3' end. A "regulatory sequence" is a nucleotide sequence that regulates expression of a coding sequence to which it is operably linked. Non-limiting examples of regulatory sequences include promoters, enhancers, transcription initiation sites, translation start sites, translation stop sites, and transcription terminators. The term "operably linked" refers to a juxtaposition of components such that they are in a relationship permitting them to function in their intended manner. A regulatory sequence is "operably linked" to a coding region when it is joined in such a way that expression of the coding region is achieved under conditions compatible with the regulatory sequence.

As used herein, a "polycistronic mRNA" refers to a transcription product that includes two or more coding regions. Expression of the two or more coding regions is controlled by a single promoter, and the series of the two or more coding regions that are transcribed to produce a polycistronic mRNA is referred to as an operon.

As used herein, "genetically modified bacterium" refers to a bacterium that has been altered "by the hand of man." A genetically modified bacterium includes a bacterium into which an exogenous polynucleotide, for example, an expression vector, has been introduced.

As used herein, a "vector" is a replicating polynucleotide, such as a plasmid, to which another polynucleotide may be attached so as to bring about the replication of the attached polynucleotide.

As used herein, an "exogenous protein" and "exogenous polynucleotide" refers to a protein and polynucleotide, respectively, which is not normally or naturally found in a microbe, and/or has been introduced into a microbe. An exogenous polynucleotide may be separate from the genomic DNA of a cell (for example, it may be a vector, such as a plasmid), or an exogenous polynucleotide may be integrated into the genomic DNA of a cell.

As used herein, a "heterologous" polynucleotide, such as a heterologous promoter, refers to a polynucleotide that is not normally or naturally found in nature operably linked to another polynucleotide, such as a coding region. As used herein, a "heterologous" protein or "heterologous" amino acid refers to amino acids that are not normally or naturally found in nature flanking an amino acid sequence.

As used herein, a protein may be "structurally similar" to a reference protein if the amino acid sequence of the protein possesses a specified amount of sequence similarity and/or sequence identity compared to the reference protein. Thus, a protein may be "structurally similar" to a reference protein if, compared to the reference protein, it possesses a sufficient level of amino acid sequence identity, amino acid sequence similarity, or a combination thereof.

Structural similarity of two proteins can be determined by aligning the residues of the two proteins (for example, a candidate protein and any appropriate reference protein described herein) to optimize the number of identical amino acids along the lengths of their sequences; gaps in either or both sequences are permitted in making the alignment to optimize the number of identical amino acids, although the amino acids in each sequence must nonetheless remain in their proper order. A reference protein may be a protein described herein. A candidate protein is the protein being compared to the reference protein. A candidate protein may be isolated, for example, from a microbe, or can be produced using recombinant techniques, or chemically or enzymatically synthesized.

Unless modified as otherwise described herein, a pairwise comparison analysis of amino acid sequences can be carried out using the Blastp program of the BLAST 2 search algorithm, as described by Tatiana et al., FEMS Microbiol. Lett., 1999; 174:247-250, and available on the National Center for Biotechnology Information (NCBI) website. The default values for all BLAST 2 search parameters may be used, including matrix=BLOSUM62; open gap penalty=11, extension gap penalty=1, gap x_dropoff=50, expect=10, wordsize=3, and filter on. Alternatively, polypeptides may be compared using the BESTFIT algorithm in the GCG package (version 10.2, Madison Wis.).

In the comparison of two amino acid sequences, structural similarity may be referred to by percent "identity" or may be referred to by percent "similarity." "Identity" refers to the presence of identical amino acids. "Similarity" refers to the presence of not only identical amino acids but also the presence of conservative substitutions.

Thus, as used herein, a candidate protein useful in the methods described herein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence similarity to a reference amino acid sequence.

Alternatively, as used herein, a candidate protein useful in the methods described herein includes those with at least 50%, at least 55%, at least 60%, at least 65%, at least 70%, at least 75%, at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to the reference amino acid sequence.

Conditions that are "suitable" for an event to occur, such as expression of an exogenous polynucleotide in a cell to produce a protein, or production of a product, or "suitable" conditions are conditions that do not prevent such events from occurring. Thus, these conditions permit, enhance, facilitate, and/or are conducive to the event.

As used herein, an "animal" includes members of the class Mammalia and members of the class Ayes, such as human, avian, bovine, caprine, ovine, porcine, equine, canine, and feline.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The terms "comprises" and variations thereof do not have a limiting meaning where these terms appear in the description and claims.

Unless otherwise specified, "a," "an," "the," and "at least one" are used interchangeably and mean one or more than one.

Also herein, the recitations of numerical ranges by endpoints include all numbers subsumed within that range (for example, 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

Reference throughout this specification to "one embodiment," "an embodiment," "certain embodiments," or "some embodiments," etc., means that a particular feature, configuration, composition, or characteristic described in connection with the embodiment is included in at least one embodiment of the disclosure. Thus, the appearances of such phrases in various places throughout this specification are not necessarily referring to the same embodiment of the disclosure. Furthermore, the particular features, configurations, compositions, or characteristics may be combined in any suitable manner in one or more embodiments.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

BRIEF DESCRIPTION OF THE FIGURES

FIG. 2A shows an exemplary expression/secretion vector. In some embodiments, the vector can be used to express Lysin 2 (Lys2) and Lysin 3 (Lys3) in *Lactococcus lactis*. The vector drives expression of inserted genes via a chloride-inducible promoter (CIP) $P_{gad}$ (Geldart et al. Antimicrob Agents Chemother. 2017; 61(4):e02033-16). $P_{gadR}$ is a constitutive promoter controlling the production of the activator protein GadR which activates the $P_{gad}$; Cm is chloramphenicol; RepA=a replication gene for *E. coli* plasmid replication; RepC=a replication gene for Streptococcal plasmid replication. Genes to be expressed are cloned downstream of $P_{gad}$. FIG. 2B shows a schematic of exemplary Lys2 and Lys3 genes fused to the high-efficiency *L. lactis* signal peptide SLPmod. FIG. 2C shows an exemplary amino acid sequence of Lys2 (SEQ ID NO:1). FIG. 2D shows an exemplary amino acid sequence of Lys3 (SEQ ID NO:2).

FIG. 3A-FIG. 3C show lytic activity of Lys2 and Lys3 from supernatants of engineered *L. lactis*. Filter-sterilized supernatants collected as indicated in Example 1 were introduced to CP suspensions. FIG. 3A. These enzymes hydrolyze peptidoglycan in the cell wall resulting in cell lysis and decreased optical density. FIG. 3B. Cp ATCC 12916 (CP12) was exposed to either 33% supernatant from Lys3 secreting *L. lactis* or a control supernatant with no antimicrobial peptide (AMP) expression. FIG. 3C. CP strains Cp ATCC 12916 (CP12), Cp ATCC 13124 (CP13), Cp WT Cp26 (CP26), and Cp WT Cp39 (CP39) were exposed to 33% supernatant from Lys2 secreting *L. lactis* or a control supernatant with no AMP expression. Error bars show standard errors; n=3.

FIG. 4 shows an adaptation of a method using microfluidic co-encapsulation of antimicrobial protein producer and target pathogen (Scanlon et al. Biotechnol. Bioeng. 2014, 111:232-243) for use with *L. lactis* and CP. A mutagenic library is first constructed in *L. lactis,* 1, mixed with CP in low-gel agarose, 2, and encapsulated via a microfluidic device, 3. Droplets are solidified and incubated in-emulsion to allow AMP production, and washed with appropriate fluorescent dyes to indicate activity, 4. Droplets are sorted via fluorescent-activated cell sorting, 5, enriching for droplets with higher total activity. Secretion rate can then be decoupled from per-molecule activity via HPLC for top clones, 6.

FIG. 5 shows exemplary thermal response of the lysins of Example 4. $k_i$ for each sample was determined and normalized for each lysin by the maximum value observed (see Table 1).

FIG. 6 shows a multiple-sequence alignment of the catalytic domain of Lys2 (SEQ ID NO:7), Lys2ConCat (SEQ ID NO:3), and Lys2Con20Cat (SEQ ID NO:4). (*) indicates identical amino acids, (:) indicates conservation between strongly similar groups, (.) indicates conservation between weakly similar groups, ( ) indicates amino acids that are not related. Clustal Omega with standard settings was used for all multiple sequence alignments (available on the world wide web at ebi.ac.uk/Tools/msa/clustalo/).

FIG. 7 shows a sequence alignment of cell wall binding domain (CWBDs) of Lys2 (SEQ ID NO:9) and the CWBD of Lys3 (SEQ ID NO:10). (*) indicates identical amino acids, (:) indicates conservation between strongly similar groups, (.) indicates conservation between weakly similar groups, ( ) indicates amino acids that are not related. Clustal Omega with standard settings was used for all multiple sequence alignments (available on the world wide web at ebi.ac.uk/Tools/msa/clustalo/).

FIG. 8 shows a multiple-sequence alignment of the catalytic domain of Lys2 (SEQ ID NO:7), the catalytic domain of Lys3 (SEQ ID NO:8), the catalytic domain of Lys2Con (SEQ ID NO:3), and the catalytic domain of Lys2Con20 (SEQ ID NO:4). (*) indicates identical amino acids, (:) indicates conservation between strongly similar groups, (.) indicates conservation between weakly similar groups, ( ) indicates amino acids that are not related. Clustal Omega with standard settings was used for all multiple sequence alignments (available on the world wide web at ebi.ac.uk/Tools/msa/clustalo/).

DETAILED DESCRIPTION

In some aspects, this disclosure describes a vector, a genetically modified bacterium including the vector, methods of making the bacterium, methods of using the bacterium, and kits including the bacterium. In some embodiments, the vector and/or the genetically engineered bacterium are preferably suitable for the treatment and/or control of a pathogenic microbe including, for example, *Clostridium perfringens* (CP).

In another aspect, this disclosure describes a lysin catalytic domain generative model and novel lysin catalytic domains and lysins generated, at least in part, using the lysin catalytic domain generative model.

*Clostridium perfringens* (CP)

Figure 1:
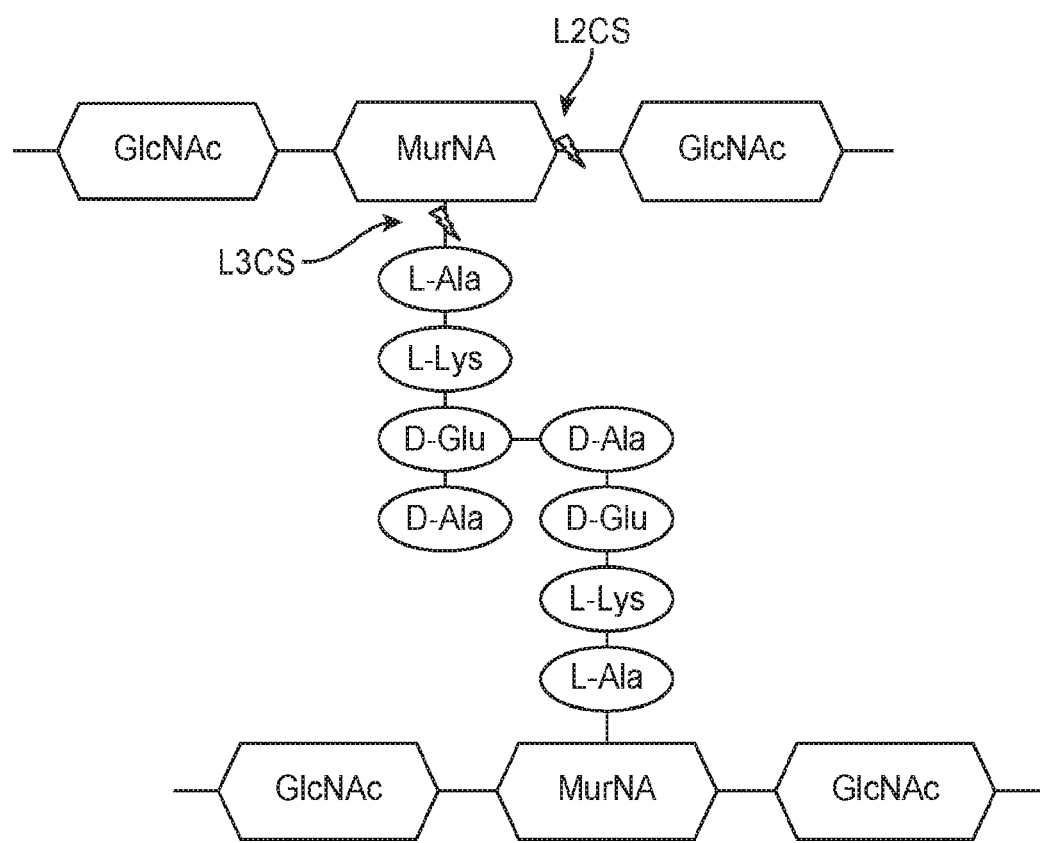
FIG. 1 shows a schematic structure of a gram-positive peptidoglycan with the putative cleavage sites of Lysin 2 (cleavage site: L2CS), a predicted muramidase, and Lysin 3 (cleavage site: L3CS), a predicted N-acetylmuramoyl-L-alanine amidase.
Figure 4:
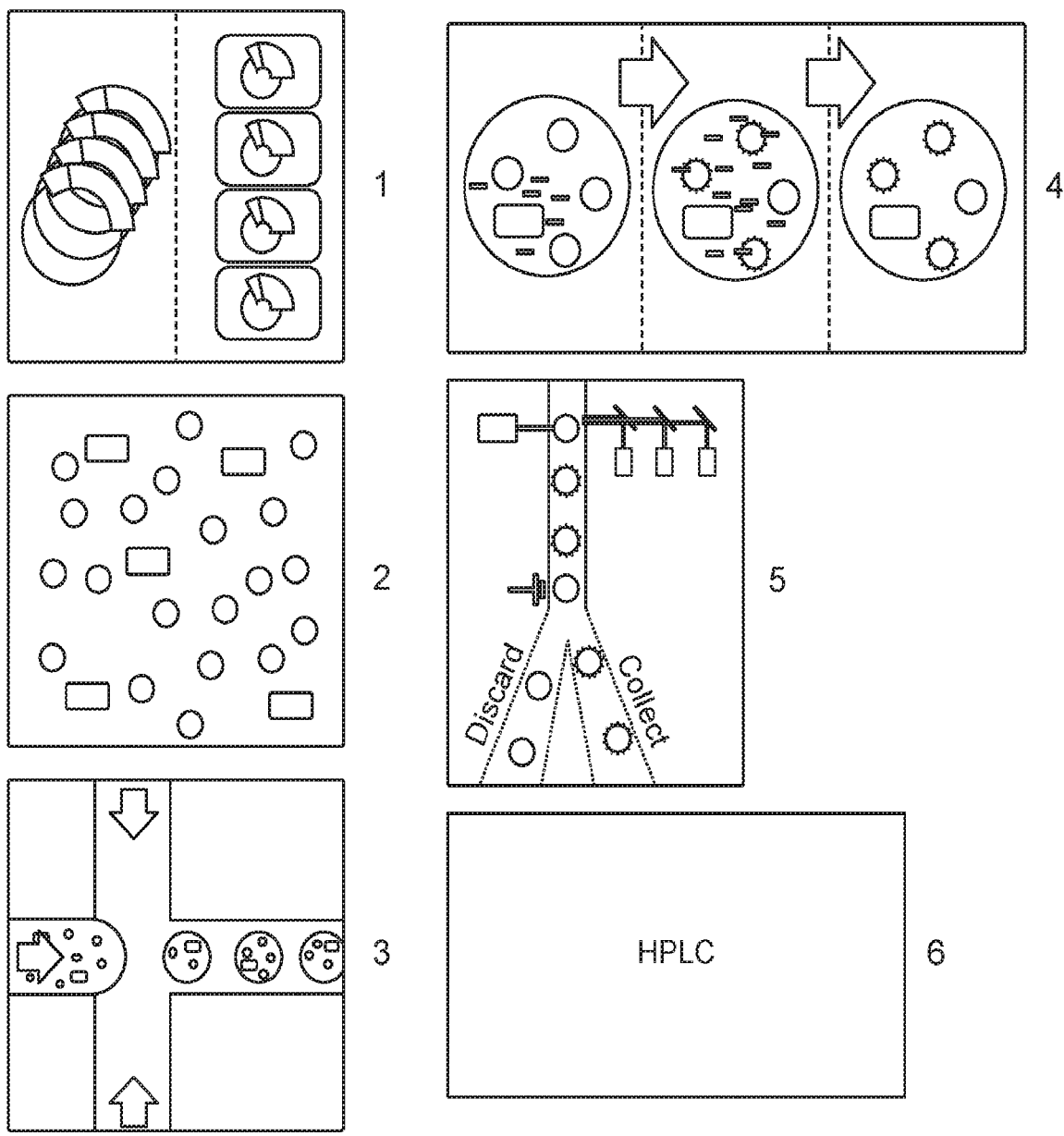
Figure 5:
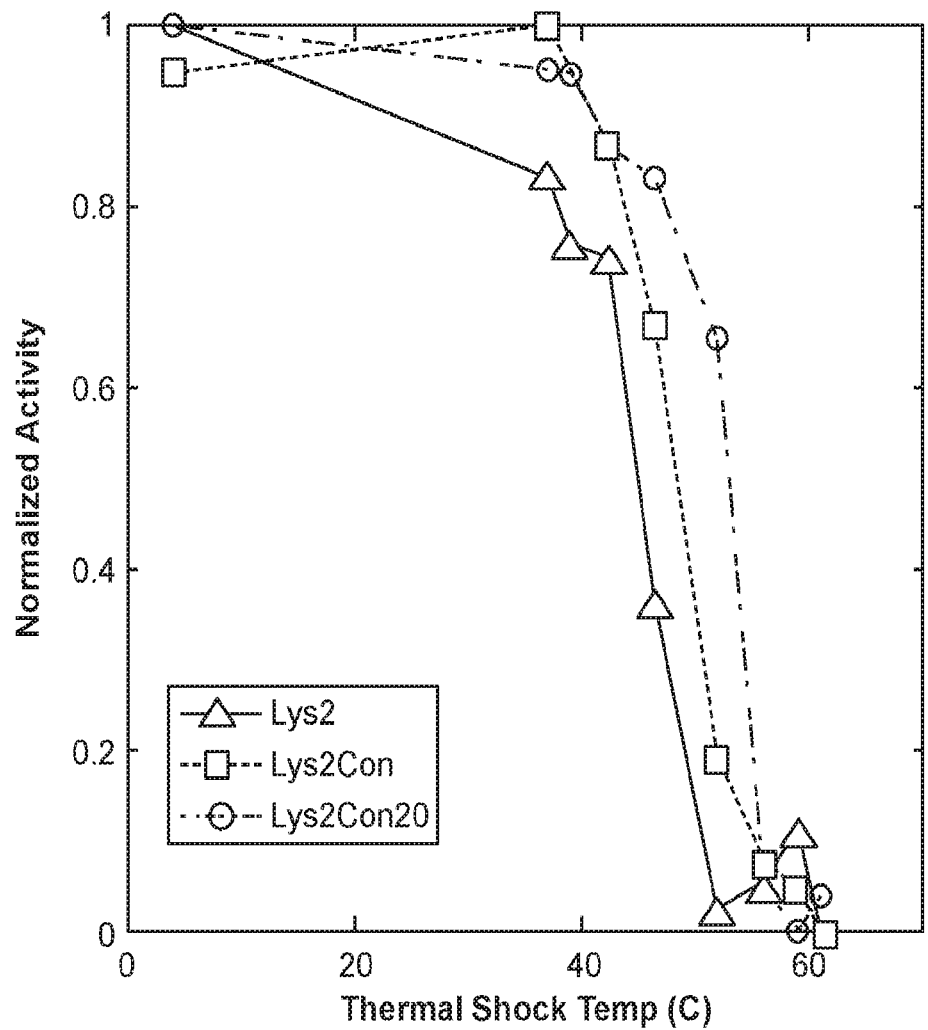

*Clostridium perfringens* (CP) is a bacterial pathogen that exerts great pressure on poultry producers. CP is a Gram-positive, gas-producing, rod-shaped bacterium that causes necrotic enteritis (NE) in poultry, resulting in billions of dollars in lost product worldwide (McDevitt et al., Worlds. Poult. Sci. J. 2006; 62:221; Savva et al., J. Biol. Chem. 2013; 288: 3512-3522; M'Sadeq, et al., Anim. Nutr. 2015; 1:1-11; Miller et al., Avian Dis. 2010; 54(1):33-40; Glisson et al. Avian Dis. 2004; 48(3):658-62; Zhang et al., Avian Dis. 2010; 54(4):1298-300. Scallan et al., Emerg. Infect. Dis. 2011; 17:7-15; Official Publication of the Association of American Feed Control Officials (AAFCO), 2016). Different strains of CP accomplish this virulence through the production of 5 total endotoxins as well as a pore-forming toxin, NetB (Savva et al., J. Biol. Chem. 2013; 288: 3512-3522).

CP infections increase as the use of agricultural antibiotics decrease. In addition, CP can cause illness in humans as a foodborne infection, and an estimated 900,000 cases in humans occur in the United States per year (Scallan et al., Emerg. Infect. Dis. 2011; 17:7-15). Products with high efficacy and specificity are needed to control CP outbreaks and prevent product loss.

In some embodiments, the genetically engineered bacteria described herein may be used to reduce pathogenic CP in poultry. In some embodiments, the pathogenic CP can include at least one of the following CP strains: Cp ATCC 12916 (CP12), Cp ATCC 13124 (CP13), Cp WT Cp26 (CP26), Cp WT Cp39 (CP39), and *Clostridium perfringens* B str. ATCC 3626.

Genetically Modified Bacterium

In some embodiments, a genetically modified bacterium includes a modification that allows it to express and/or deliver an antimicrobial peptide (AMP) to the gastrointestinal (GI) tract of a subject.

In some embodiments, the genetically modified bacterium includes a probiotic bacterium. In some embodiments, the genetically modified bacterium includes a *Lactococcus* spp. or a *Lactobacillus* spp. In some embodiments, the genetically modified bacterium includes at least one of *Lactococcus lactis* NZ9000 (*L. lactis*), *Escherichia coli* Nissle 1917, *Lactobacillus acidophilus*, *Lactobacillus reuteri*, *Lactobacilus bulgaricus*, and *Bacillus subtillis*.

*Lactobacillus acidophilus*, *Lactobacillus bulgaricus*, *Lactobacillus reuteri*, *Enterococcus faecium*, and *Bacillus subtilis* are considered direct-fed microbial products (DFMs) and are generally regarded as safe to consume (GRAS). DFMs are purported to contain live (viable) microorganisms. The Official Publication of the Association of American Feed Control Officials (AAFCO), under Section 36 Fermentation Products, defines animal feed ingredients derived from spent fermentation processes. For regulatory purposes, direct-fed microbial products are considered a subclass of fermentation or yeast products because they are similarly produced. A direct-fed microbial product listed by the AAFCO Official Publication and labeled with the AAFCO-approved label statement for live microorganism content, and not labeled or promoted with any therapeutic or structure/function claims, will be regulated as a food as defined in Section 201(f)(3) and may not require FDA regulatory attention.

In some embodiments, the genetically modified bacterium preferably includes *L. lactis*.

Antimicrobial Proteins (AMPs)

In some embodiments, the genetically modified bacterium expresses an antimicrobial peptide (AMP). An AMP has antimicrobial activity that inhibits or kills a target microbe (including, for example, a pathogenic microbe such as CP). AMPs may offer a number of advantages over more traditional antibiotic counterparts.

Traditional antibiotics are often small secondary metabolites that are stable and that exhibit broad-spectrums of activity. As a result of these qualities, traditional antibiotics are easy to administer and cheap to produce. However, their broad-spectrum of activity leads to both the clearance of commensal organisms which compose the complex microflora in areas such as the gastrointestinal (GI) tract; leading to secondary infections by opportunistic pathogens such as *Enterococcus faecium* and *Clostridium difficile*. In addition to these problems, broad-spectrum activity elicits a selective pressure across many off-target organisms, increasing the likelihood of the development of genetic clusters which provide resistance and can be subsequently transferred via horizontal gene transfer to other organisms.

AMPs may address these concerns because they often have very narrow activity spectrums and only affect target or closely related organisms. However, AMPs are often rapidly degraded in areas such as the GI tract, a feature that has historically limited their use.

In some embodiments, the genetically modified bacterium may be designed to secrete an AMP. As further discussed herein, in some embodiments, the AMP can be secreted within a microenvironment of interest, overcoming delivery barriers including rapid degradation that have previously limited the use of AMPs.

In some embodiments, the AMP includes a lysin.

A lysin (also referred to as an endolysin) is an enzymatic AMP generally having two domains. One domain provides catalytic activity and one domain provides specificity (e.g., binding to particular Gram-positive organisms); the domains are traditionally arranged N-terminally and C-terminally, respectively (Borysowski, et al., Exp. Biol. Med. 2006; 231:366-377; Pastagia et al., J. Med. Microbiol. 2013; 62:1506-1516; Schmitz et al., Appl. Microbiol. Biotechnol. 2011; 89:1783-95). The catalytic domain is a peptidoglycan hydrolase which may specifically cleave one of the bonds found within a peptidoglycan, the primary structural building block found within the cell walls of Gram-positive organisms. The domain providing specificity is sometimes referred to as a cell wall binding domain.

Lysins can degrade the cell walls of target bacteria with high activity and specificity (Borysowski, et al., Exp. Biol. Med. 2006; 231:366-377; Pastagia et al., J. Med. Microbiol. 2013; 62:1506-1516). This degradation continues until the osmotic pressure across the membrane exceeds the limit of the degraded cell wall, resulting in cell lysis. The specificity of these proteins may be enabled by interactions with unique peptidoglycan modifications on the cell wall. These modifications enable bacteriophage, the biological origin of endolysins, to lyse only their host bacterium even in complex environments such as the GI tract. In addition to this high specificity, rate of resistance emergence towards endolysins is very low. Previous efforts with staphylococci, pneumococci, and *Bacillus cereus* were unable to produce mutants with endolysin-resistance in the laboratory (Pastagia et al., J. Med. Microbiol. 2013; 62:1506-1516).

In some embodiments, the lysin includes at least one of Lys2 and Lys3. Lys2 is a muramidase, and Lys3 is a N-acetylmuramoyl-L-alanine amidase. Both lysins use a pair of SH3 binding domains that may provide specificity through binding to the peptidoglycan of *Clostridium perfringens* with high specificity.

Although Lys2 and Lys3 were previously identified as putative lysins through a bioinformatic analysis of multiple CP genomes (Schmitz et al., Appl. Microbiol. Biotechnol. 2011; 89:1783-95), Lys2 and Lys3 were among many putative lysins identified, and, at the time of the invention, their function and specificity had not been experimentally verified. Moreover, not all of the previously identified putative lysins showed activity against *Clostridium perfringens*. For example, neither Lys1 (PlyCM (characterized in Schmitz et al., Appl. Microbiol. Biotechnol. 2011; 89:1783-95)) or Lys4 (Genbank Accession No. ZP_02630819) showed activity in an initial screen.

In some embodiments, Lys2 includes the amino acid sequence SEQ ID NO:1. In another embodiment, Lys2 includes an amino acid sequence that is structurally similar to SEQ ID NO:1.

In some embodiments, Lys3 includes the amino acid sequence SEQ ID NO:2. In another embodiment, Lys3 includes an amino acid sequence that is structurally similar to SEQ ID NO:2.

In some embodiments, the AMP includes the catalytic domain of a lysin. In some embodiments, the AMP includes a sequence having at least 80%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence homology to the catalytic domain of at least one of Lysin 2 (Lys2), Lysin 3 (Lys3), Lys2Con (SEQ ID NO:5) or Lys2Con20 (SEQ ID NO:6). In some embodiments, the catalytic domain of Lys2Con includes Lys2ConCat (SEQ ID NO:3). In some embodiments, the catalytic domain of Lys2Con20 includes Lys2Con20Cat (SEQ ID NO:4).

In some embodiments, the lysin catalytic domain may be generated using a lysin catalytic domain generative model as described herein. For example, in some embodiments the lysin may include Lys2ConCat (SEQ ID NO:3) or Lys2Con20Cat (SEQ ID NO:4). In some embodiments, a lysin including the lysin catalytic domain generated using a generative model can demonstrate improved thermal stability and/or improved lytic activity relative to a wild type lysin.

In some embodiments, the AMP may include an AMP described in U.S. Patent Publication No. 2016-0279175 including, for example, a Type IIa bacteriocin. A Class IIa bacteriocin can include, for example, Enterocin A, Hiracin JM79, and Enterocin P. In some embodiments, the AMP may include an AMP described in Table 2 of U.S. Patent Publication No. 2016-0279175.

Lysin Catalytic Domain Generative Model

A lysin catalytic domain generative model may be used to generate a model-generated lysin catalytic domain having a model-generated lysin catalytic domain sequence. In some embodiments, a model-generated lysin catalytic domain demonstrates improved physical properties over a wild type lysin catalytic domain and/or a lysin including the model-generated lysin catalytic domain demonstrates improved physical properties over a lysin including the wild type lysin catalytic domain. The improved physical properties can include, for example, improved thermal stability, improved lytic activity, improved chemical stability, improved stability in low pH, improved stability in environments of high bile concentrations, improved stability against proteolysis, improved solubility, and/or lower immunogenicity.

In some embodiments, a lysin catalytic domain generative model includes generation of a guide sequence; identification of mutable sequence positions in the guide sequence; generation of a structurally-guided multiple sequence alignment; generation of a reduced multiple sequence alignment; and generation of a model-generated lysin catalytic domain. Particular implementations of this methodology can be accomplished by using any suitable computational tool or tools with the necessary characteristics or functionalities.

In some embodiments, generation of a guide sequence and identification of mutable sequence positions in the guide sequence can include aligning two or more lysin catalytic domain sequences. In some embodiments, the lysin catalytic domain sequences to be aligned may be selected from sequences having a taxonomic label of an organism against which the lysin is to be generated. In some embodiments, the organism against which the lysin is to be generated can include a Gram-positive organism including, for example, *Enterococcus faecium, Enterococcus faecalis, Clostridium difficile, Clostridium perfringens, Staphylococcus aureus*, and/or *Streptococcus pneumoniae*. In some embodiments, the organism against which the lysin is to be generated preferably includes *Clostridium perfringens*.

In some embodiments, the lysin catalytic domain sequences can be selected by identifying sequences homologous to a known lysin catalytic domain. In some embodiments, identifying sequences homologous to a known lysin catalytic domain may be identified using a sequence similarity search tool including, for example, Jackhmmer, PSI-BLAST, PSI-Search, etc.

In some embodiments, the lysin catalytic domain sequences to be aligned may be obtained from a protein sequence database including, for example, UniProt, Swiss-Prot, Pfam, InterPro, PEDANT, PROSITE, ProDom, etc.

In some embodiments, the lysin catalytic domain sequences may be aligned using a structurally-guided multiple sequence aligner including, for example, the PROMALS3D, T-COFFEE, MAFFT, etc.

In some embodiments, a consensus sequence derived from the multiple sequence alignment may form a seed sequence. In some embodiments, a model-generated lysin catalytic domain sequence may include the seed sequence. For example, as described in Example 4, a model-generated lysin catalytic domain sequence can include the seed sequence Lys2ConCat (SEQ ID NO:3).

Additionally or alternatively, a non-gapped sequence position of the seed sequence may be used to determine a mutable position or a set of mutable positions. For example, a non-gapped sequence position in a seed sequence exhibiting site diversity above some tunable threshold may be used to select a set of mutable positions.

In some embodiments, one or more additional lysin catalytic domain sequences with either homology to the seed sequence, or homology with a curated database of lysin catalytic domain family members, may be acquired from a protein sequence database. In some embodiments, identifying sequences homologous to the seed sequence may be identified using a sequence similarity search tool including, for example, Jackhmmer, PSI-BLAST, PSI-Search, etc.

In some embodiments, lysin catalytic domain family members may have a taxonomic label within a phylum of the organism against which the lysin is to be generated. For example, when the organism against which the lysin is to be generated includes *Clostridium difficile, Clostridium perfringens, Enterococcus faecium, Enterococcus faecalis, Staphylococcus aureus*, and/or *Streptococcus pneumoniae*, the phylum may include Firmicutes.

Once identified, such additional sequence may be used in addition to the seed sequence to generate a second multiple sequence alignment using a structurally-guided multiple sequence aligner. In some embodiments, the sequences may be aligned using a structurally-guided multiple sequence aligner including, for example, PROMALS3D, T-COFFEE, MAFFT, etc.

In some embodiments, the non-gapped position of the seed sequence within the second multiple sequence alignment may be identified. In some embodiments, the frequencies of amino acid occurrences at these positions can be bias-corrected. Such bias-correction can account for systemic sampling biases (e.g., particular types of bacteria which happen to be genome-sequenced more often due) or phylogenetic biases.

In some embodiments, non-gapped positions identified by using a structurally-guided multiple sequence aligner to align the seed sequence and other lysin catalytic domain family members may be used as the basis for statistical model fitting. Statistical model fitting may include, for example, determining sitewise, pairwise, and/or higher order interaction character occurrence frequencies (e.g., amino acids, gaps, etc.) and/or energy contributions. In some embodiments, statistical model fitting may include application of a Potts model (Wu, Rev. Mod. Phys. 1982; 54:235). In some embodiments, statistical model fitting preferably includes regularization (e.g., employing penalties during optimization to avoid problems of overfitting) and statistical approximations (e.g., application of a pseudo-likelihood approximation). In some embodiments, residue interaction selection may be made based on proximity in a homology model of the guide sequence. In some embodiments, residue interaction selection may be used to reduce the fitted parameter set (including, for example, the identification of experimentally verified catalytic residues).

In some embodiments, a statistical model incorporating parameters describing sitewise, pairwise, and/or higher order interactions may be fit to the bias-corrected character occurrence frequencies. In some embodiments, the statistical model preferably returns a statistical fitness score. In some embodiments, the inference parameters of a statistical model may be applied to describe bias-corrected, positional, amino acid frequency data within the multiple sequence alignment.

In some embodiments, generation of a model-generated lysin catalytic domain includes generation of a set of model-generated lysin catalytic domain sequences.

For example, an integer programming optimization scheme (e.g., a MATLAB script) may be used to generate sequences with statistical fitness scores greater than the seed sequence by allowing in silico mutations at positions of the seed sequence designated mutable positions. Additional physical properties can be applied as constraints to the optimization process to steer towards sequences with desired traits, such as net charge and/or another physical property.

In some embodiments, a model-generated lysin catalytic domain or a set of model-generated lysin catalytic domain sequences may be selected for experimental verification. Experimental verification may be done in any appropriate context. For example, verification may include determining the effect of a model-generated lysin catalytic domain only and/or using a full-length lysin that incorporates the model-generated lysin catalytic domain. For example, a full-length lysin may include the sequence of a cell wall binding domain (either from a naturally occurring or a synthetic lysin) and a model-generated lysin catalytic domain.

An example of a lysin catalytic domain generative model implementation, used to generate the lysin catalytic domains Lys2ConCat and Lys2Con20Cat, is described in Example 4.

Protein Expression System (Vector)

In another aspect, this disclosure describes a vector. In some embodiments, the vector is included in the genetically modified bacterium.

In some embodiments, the vector can include a shuttle vector. In some embodiments, the vector can include pNZC (FIG. 2), pBF25 (Forkus et al., Sci Rep. 2017 Jan. 17; 7:40695), pMPES (Geldart et al. Pharmaceuticals (Basel) 2016; 9(4):60), or pLIKE:pveg:GFP (original vector backbone from: Toymentseva et al., Microbial Cell Factories, 2012, 11:143; with the pveg promoter and GFP cassette from Guiziou et al., Nucleic Acids Research, 2016, 44(15):7495-508).

In some embodiments, the vector includes at least one of a heterologous promoter; an inducible promoter; a constitutive promoter (including, for example, a constitutive promoter controlling the activation of the inducible protomer); an antibiotic resistance gene, or other gene to stabilize plasmid expression in a given environment or host bacteria; and a replication gene controlling replication in a host organism. In some embodiments, the vector may further include a genetic element that destabilizes a vector outside of a particular environment.

In some embodiments, the vector provides AMP expression. For example, in some embodiments, the vector includes a coding region encoding one or more AMPs.

In some embodiments, as further discussed herein, a coding region of the vector may encode at least one of a signal peptide, a modulator protein, and a protein (e.g., an antibiotic) to stabilize plasmid expression in a given environment or host bacteria.

Secretion and Signal Peptide

In some embodiments, the coding region encoding an AMP can be operably linked to a coding region encoding a signal peptide. In some embodiments, the coding regions are operably linked such that the signal peptide and the AMP are expressed as a single protein. For example, the N-terminus of an AMP can be fused to a signal peptide. In one embodiment, the signal peptide directs the AMP to the secretory pathway.

Examples of secretion signaling peptides useful in lactic acid bacteria, including *L. lactis, Lb. acidophilus, Lb. acidophilus, Lb. bulgaricus, Lb. reuteri*, and *Lb. plantarum* are known. For example, in some embodiments, the signal peptide can include the high-efficiency *L. lactis* signal peptide SLPmod as described by Fernandez et al., Appl Environ Microbiol. 2009, 75(3):869-71.

Another example of a useful secretion signal peptide is from the protein Usp45 (Van Asseldonk et al., Gene 1990, 95, 155-160). Several variations on Usp45 have been explored and may also be employed (Ng and Sarkar, Appl. Environ. Microbiol. 2012, 79:347-356).

Additionally, *lactobacillus* signal peptides including but not limited to Lp_3050 and Lp_2145 may be used in *L. lactis* and Lactobacilli spp.

Other signal peptides can be selected by a person having skill in the art including, for example, from annotated databases of proteins from *L. lactis* or an annotated database of another target host species.

Heterologous Promoter

In some embodiments, expression of a coding region of the vector (including, for example, expression of a coding region encoding AMP) may be controlled by a heterologous promoter. Such heterologous promoters may confer important advantages including, for example, that cell mass can increase substantially before protein production is turned on, and that the antimicrobial protein itself does not inhibit cell growth.

Libraries of regulatable promoters in bacteria have been previously constructed and characterized (see, e.g., Schmitz et al., Appl. Microbiol. Biotechnol. 2011; 89:1783-95; Forkus et al., Sci Rep. 2017 2017; 7:40695; Geldart et al. Pharmaceuticals (Basel) 2016; 9(4):60; Geldart et al., Antimicrob. Agents Chemother. 2017; 61(4):e02033-16; Geldart et al., Appl. Environ. Microbiol. 2015; 81(11):3889-97; Borrero et al. ACS Synth Biol. 2015; 4(3):299-306). For example, at least three expression systems have been used in probiotics: I) a chloride-inducible promoter $P_{gad}$ (Geldart et al. Antimicrob Agents Chemother. 2017; 61(4):e02033-16), II) a ProTeOn+system (Forkus et al., Sci Rep. 2017 2017; 7:40695; Volzing et al., ACS Synth Biol. 2013; 2(11):643-50), and III) constitutive promoters. (See, e.g., U.S. Patent Publication Nos. 2015/0265660, 2016/0279175).

In some embodiments, the heterologous promoter is a chloride-inducible promoter. A chloride-inducible promoter can include, for example, $P_{gad}$. $P_{gad}$ has been found to turn on protein expression when chloride concentration reaches 0.1M—a similar chloride concentration as that found in the stomach of animals (Geldart et al. Antimicrob Agents Chemother. 2017; 61(4):e02033-16).

In some embodiments, the heterologous promoter includes a ProTeOn+system. Prokaryotic-TetOn (ProTeOn) and prokaryotic-TetOn (ProTeOff) are described in Volzing et al., ACS Chem. Biol., 2011; 6:1107-1116. These proteins are designed to work with a heterologous promoter that optimizes interactions between domains in ProTeOn and ProTeOff to result in high levels of expression of operably linked transcription units. The ProTeOn protein contains an inducible binding domain (the reverse tetracycline repressor rTetR), which binds to a tetracycline operator sequence in the presence of an inducer such as tetracycline, doxycycline, or anhydrous tetracycline (aTc). ProTeOff includes the tetracycline repressor, TetR, instead of rTetR. rTetR and TetR undergo conformational changes upon binding to an inducer, which cause them to sensitively dissociate and associate from the tetracycline operator site, respectively. Thus, the TetR of ProTeOff is designed to strongly bind to DNA in the absence of aTc and drive expression, and the aTetR of ProTeOn is designed to strongly bind to DNA in the presence of aTc and drive expression.

An additional positive feedback effect is observed with the use of ProTeOn+—with the activator protein (ProTeOn) activating its own expression by binding to the engineered DNA promoter site (Pon) that includes tetracycline and LuxR operator binding regions and is operably linked to a coding region encoding ProTeOn—strongly increasing the expression of AMPs (Forkus et al., Sci Rep. 2017 2017; 7:40695; Volzing et al., ACS Synth Biol. 2013; 2(11):643-50). Compared to commercially available strong DNA promoters, a ProTeOn+system demonstrates extraordinarily strong promoter activity in *E. coli* without the use of an inducer. For example, ProTeOn+ was found to be double the strength of oxb20, one of the strongest commercially available promoters for *E. coli*.

Additional Coding Regions

The vector may optionally include an additional coding region (that is, a coding region in addition to the coding region encoding an AMP) that is operably linked to a second promoter, where the additional coding region encodes a modulator protein that regulates the expression of the heterologous promoter controlling AMP expression. A modulator protein is a protein that modulates expression of a transcription unit operably linked to a heterologous promoter. In one embodiment, a modulator protein binds to a promoter or to other nucleotides around the promoter and modulates expression of a coding region operably linked to that promoter. In one embodiment, the modulator protein may either induce or prevent expression of the operably linked coding region in the presence of a modulating agent. An example of a modulator protein that controls expression of a chloride-inducible promoter is the activator protein GadR. An example of a sequence of a GadR protein is provided by Genbank Accession No. ADJ60177.

Examples of modulator proteins that bind to a tetracycline-inducible promoter are known in the art and include tetracycline repressor proteins, and reverse tetracycline repressor proteins. In one embodiment, a modulator protein can include ProTeOn or ProTeOff.

The proteins described herein, including the proteins expressed by coding regions of the vector (for example, an antimicrobial protein and/or a modulator protein) may include conservative amino acid substitutions. In one embodiment, a protein described herein can include at least one, at least two, at least three, at least four, or at least five conservative substitutions. In some embodiments, a protein described herein is structurally similar to a reference protein, such as a modulatory protein or an antimicrobial peptide.

Without wishing to be bound by theory, it is believed that the combination of using two lysins; operably linking a coding region encoding an AMP to a coding region encoding a signal peptide; and using a heterologous promoter provides a vector with improved properties. For example, previous attempts to engineer *Lactobacillus johnsonii* to secrete an anti-*Clostridium perfringens* lysin (Gervasi et al. Letters in Applied Microbiology 2014; 59(4):355-361) had inconsistent results but used a single enzymatic class of lysin, used a nisin-inducible promoter for expression, and included no engineering of secretion.

Construction and Introduction of the Vector

Construction of vectors described herein may employ standard ligation techniques known in the art. See, for example, Sambrook et al., 1989. Molecular cloning: a laboratory manual, 2nd ed. Cold Spring Harbor Laboratory Press, Cold Spring Harbor, N.Y. Selection of a vector depends upon a variety of desired characteristics in the resulting construct, such as a selection marker, vector replication rate, and the like. Vectors can be introduced into a host cell using methods that are known and used routinely by the skilled person. The vector may replicate separately from the chromosome present in the microbe, or the polynucleotide may be integrated into a chromosome of the microbe. A vector introduced into a host cell optionally includes one or more marker sequences, which typically encode a molecule that inactivates or otherwise detects or is detected by a compound in the growth medium. For example, the inclusion of a marker sequence may render the transformed cell resistant to an antibiotic, or it may confer compound-specific metabolism on the transformed cell. Examples of a marker sequence include, but are not limited to, sequences that confer resistance to kanamycin, ampicillin, chloramphenicol, tetracycline, streptomycin, neomycin, and erythromycin. Generally, introduction of a vector into a host cell, origin of replication, ribosomal sites, marker sequences, and other aspects of vectors may vary depending on whether the host cell is a Gram-positive or a Gram-negative microbe; however, these aspects of vector biology and heterologous gene expression are known to the skilled person and are routine.

Methods of Using the Vectors and Bacteria

Also provided are methods of using the vectors and genetically modified bacterium disclosed herein. The genetically modified bacterium may be present in a composition, such as a pharmaceutically acceptable formulation. In one embodiment, a formulation may be a fluid composition. Fluid compositions include, but are not limited to, solutions, suspensions, dispersions, and the like. Fluid compositions may be incorporated in the water supply of a host. In one embodiment, a formulation may be a solid composition. Solid compositions include, but are not limited to, powder, granule, compressed tablet, pill, capsule, chewing gum, wafer, and the like. Solid compositions may be incorporated in the food supply of hosts. Those formulations may include a pharmaceutically acceptable carrier to render the composition appropriate for administration to a subject. As used herein "pharmaceutically acceptable carrier" includes pharmacologically inactive compounds compatible with pharmaceutical administration. The compositions may be formulated to be compatible with its intended route of administration. A composition may be administered by any method suitable for depositing in the GI tract of a subject. Examples of routes of administration include rectal administration (for example, by suppository, enema, upper endoscopy, upper push enteroscopy, or colonoscopy), intubation through the nose or the mouth (for example, by nasogastric tube, nasoenteric tube, or nasal jejunal tube), or oral administration (for example, by a solid such as a pill, tablet, or capsule, or by liquid).

For therapeutic use, a composition may be conveniently administered in a form containing one or more pharmaceutically acceptable carriers. Suitable carriers are well known in the art and vary with the desired form and mode of administration of the composition. For example, they may include diluents or excipients such as fillers, binders, wetting agents, disintegrators, surface-active agents, glidants, lubricants, and the like. Typically, the carrier may be a solid (including powder), liquid, or combinations thereof. Each carrier is preferably "acceptable" in the sense of being compatible with the other ingredients in the composition and not injurious to the subject. The carrier is preferably biologically acceptable and inert, i.e., it permits the composition to maintain viability of the biological material until delivered to the appropriate site.

Oral compositions may include an inert diluent or an edible carrier. For the purpose of oral therapeutic administration, the active compound (e.g., the genetically modified bacterium) can be incorporated with excipients and used in the form of tablets, troches, or capsules, for example, gelatin capsules. Oral compositions can also be prepared by combining a composition of the present disclosure with a food. In one embodiment, a food used for administration is chilled. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

The active compounds can also be prepared in the form of suppositories (for example, with conventional suppository bases such as cocoa butter and other glycerides) or retention enemas for rectal delivery.

The active compounds may be prepared with carriers that will protect the compound against rapid elimination from the body, such as a controlled release formulation, including implants. Biodegradable, biocompatible polymers can be used, such as ethylene vinyl acetate, polyanhydrides, polyglycolic acid, collagen, polyorthoesters, and polylactic acid. Such formulations can be prepared using standard techniques. Liposomal suspensions can also be used as pharmaceutically acceptable carriers. These can be prepared according to methods known to those skilled in the art.

In one embodiment, a composition may be encapsulated. For instance, when the composition is to be administered orally, the dosage form is formulated so the composition is not exposed to conditions prevalent in the GI tract before the desired site, for example, high acidity and digestive enzymes present in the stomach and/or upper intestine. The encapsulation of compositions for therapeutic use is routine in the art. Encapsulation may include hard-shelled capsules, which may be used for dry, powdered ingredients, or soft-shelled capsules. Capsules may be made from aqueous solutions of gelling agents such as animal protein (for example, gelatin), plant polysaccharides or derivatives like carrageenans and modified forms of starch and cellulose. Other ingredients may be added to a gelling agent solution such as plasticizers (for example, glycerin and or sorbitol), coloring agents, preservatives, disintegrants, lubricants and surface treatment.

In one embodiment, the method includes administering an effective amount of a bacterium to a subject in need of such a genetically modified bacterium. The subject may be, for instance, human, avian (including, for instance, chickens or turkeys), bovine (including, for instance, cattle), caprine (including, for instance, goats), ovine (including, for instance, sheep), porcine (including, for instance, swine), equine (including, for instance, horses), canine (including, for instance, dogs), or feline (including, for instance, cats). The subject may be of any age. In some embodiments, the animal is preferably a domesticated bird such as a chicken or a turkey. A subject can have a gastrointestinal microflora that requires modification, such as elimination or reduction of one or more microbes. For instance, a subject may have a microbial pathogen, such as a nosocomial pathogen, present in its GI tract.

In one embodiment, the method may further include administering to the subject a modulating agent. In one embodiment, such a modulating agent will interact with the modulator protein, for example, a tet-repressor, and result in expression of the coding region encoding the antimicrobial peptide. The modulating agent may be administered to the subject before, with, or after the administration of the genetically modified bacterium, or a combination thereof.

In one embodiment, it is not necessary to administer a modulating agent to the subject. When the genetically modified bacterium includes a vector that includes a promoter such as a chloride-inducible promoter, the microbe will begin to express the AMP when it is in a suitable environment, such as the GI tract.

In one embodiment, a method includes reducing the number of pathogenic microbes. The method can include exposing a pathogenic microbe to a genetically modified bacterium described herein that expresses at least one, at least two, or at least three antimicrobial peptides. The exposure of the pathogenic microbe to multiple antimicrobial peptides increases activity and efficacy and results in a greater reduction of the pathogenic microbe than exposure to just one antimicrobial peptide. The reduction can be at least 10-fold, at least 100-fold, or at least 1000-fold. The pathogenic microbe can be in vivo (for example, inside or on the body of a subject) or in vitro (for example, not in or on the body of a subject).

In one embodiment, a method includes reducing development of resistance to antimicrobial peptides. Microbes can develop resistance to an antibiotic such as an antimicrobial peptide. For example, a population of microbes can include individuals that are resistant to an antibiotic. The use of at least two antimicrobial peptides reduces the development of resistance and the resulting regrowth of the pathogenic microbe after exposure to the antimicrobial peptides. Thus, a method can include exposing a pathogenic microbe to a genetically modified microbe described herein that expresses at least two antimicrobial peptides. Exposure of the pathogenic microbe to at least two three antimicrobial peptides results an increase in the amount of time needed for regrowth of the pathogenic microbe, a measurement of development of resistance compared to the pathogenic microbe that is exposed to only one of the antimicrobial peptides. The increase in the amount of time needed for regrowth of the pathogenic microbe can be at least 12 hours, at least 24 hours, or at least 48 hours. The pathogenic microbe can be in vivo (for example, inside or on the body of a subject) or in vitro (for example, not in or on the body of a subject).

In some embodiments, a method includes administering a genetically modified bacterium to a subject having a pathogenic microbe present in its GI tract. In one embodiment, a method includes treating a subject having a pathogenic microbe present in its GI tract. In another embodiment, the present disclosure is directed to methods for treating certain conditions in a subject that may be caused by, or associated with, a microbe. Such conditions include, for instance, Gram-negative microbial infections and Gram-positive microbial infections of the GI tract. Examples of conditions that may be caused by the presence of certain microbes in a subject's GI tract include, but are not limited to, necrotic enteritis, diarrhea, gastroenteritis, hemolytic-uremic syndrome, inflammatory bowel disease, irritable bowel disease, and Crohn's Disease.

Treating a subject, such as a subject having a pathogenic microbe or a subject having a condition, can be prophylactic or, alternatively, can be initiated after the need for treatment arises. Treatment that is prophylactic, for instance, initiated before a subject manifests symptoms of a condition caused by a pathogenic microbe, such as a member of the genus *Salmonella, Staphylococcus, Streptococcus, Clostridia, Klebsiella,* or *Enterococcus,* is referred to herein as treatment of a subject that is "at risk" of developing the condition. Typically, a subject "at risk" of developing a condition is a subject likely to be exposed to a pathogenic microbe, such as a member of the genus *Salmonella, Staphylococcus, Streptococcus* Clostridia, *Klebsiella,* or *Enterococcus,* causing the condition. For instance, the subject is present in an area where the condition has been diagnosed in at least one other subject (for example, a hospital in the case of a nosocomial infection or a farm where an infection has been detected in another animal). Accordingly, administration of a composition can be performed before, during, or after the occurrence of a condition caused by a pathogenic microbe. Treatment initiated after the development of a condition may result in decreasing the severity of the symptoms of one of the conditions, or completely removing the symptoms. In this aspect of the invention, an "effective amount" is an amount effective to prevent the manifestation of symptoms of a condition, decrease the severity of the symptoms of a condition, and/or completely remove the symptoms. The potency of a composition described herein can be tested according to routine methods (see, for instance, Stanfield et al., Microb Pathog. 1987, 3:155-165, Fox et al., Am. J. Vet. Res. 1987, 48:85-90, Ruiz-Palacios, Infect. Immun. 1981, 34:250-255, and Humphrey et al., J. Infect. Dis. 1985, 151:485-493). Methods for determining whether a subject has a condition caused by a pathogenic microbe and symptoms associated with the conditions are routine and known to the art.

The method may further include determining whether at least one symptom associated with a condition cause by a target microbe is reduced, and/or determining whether the shedding of the target microbe by the subject is reduced. Methods for determining whether a subject has a reduction in a symptom associated with a condition are routine and known in the art. Methods for measuring shedding of a microbe are likewise routine and known in the art.

Kits

In another aspect, this disclosure describes a kit. In some embodiments, the kit may include a genetically modified bacterium as described herein. In some embodiments, the kit may include a vector as described herein. In some embodiments, each of the essential materials and reagents required for treating a subject having a pathogenic microbe present in its GI tract may be assembled together in a kit. The components of the kit may be provided in an aqueous form or a dried or lyophilized form. The kit may include an instruction sheet defining administration of the genetically modified bacterium and/or the vector.

The present invention is illustrated by the following examples. It is to be understood that the particular examples, materials, amounts, and procedures are to be interpreted broadly in accordance with the scope and spirit of the invention as set forth herein.

EXAMPLES

Example 1

Materials and Methods
Bacterial Transformation and Molecular Cloning

Backbone vector pNZC (Geldart et al. Appl Environ Microbiol. 2015; 81(11):3889-97) was used for all expression and subcloning. Genes encoding for mature Lys2 and Lys3 were optimized for expression with Codon Optimization Tool (Integrated DNA Technologies, Coralville, Iowa) with target organism *Lactococcus lactis*. To the N-terminus DNA encoding for the SLPmod secretion tag was appended (Fernandez et al., Appl Environ Microbiol. 2009, 75(3):869-71), to the C-terminus DNA encoding for a 6×HIS tag (GSHHHHHH) was appended for downstream purification. These two constructs were synthesized by Integrated DNA Technologies (Coralville, Iowa) using their gBlocks platform and Gibson-assembled into the NcoI-SpeI target site of the backbone vector.

The resultant plasmids were first transformed via electroporation into MC1061 F-*Escherichia coli* (Lucigen Corporation, Middleton, Wis.), following the manufacturer's protocol and then transformed via electroporation into *L. lactis* following published protocols (Geldart et al., Appl. Environ. Microbiol. 2015; 81(11):3889-97; Borrero et al. ACS Synth Biol. 2015; 4(3):299-306).

Supernatant Production and Sterilization from *Lactococcus lactis*

*L. lactis*, engineered or control, was grown overnight without agitation at 32° C. from a fresh colony grown on BHI (Brain-heart-infusion) agar with 5 μg/mL chloramphenicol (cm). The following day, cells were washed and resuspended at an optical density (OD) of 1.0 at wavelength 600 nm in 4 mL BHI and incubated at 32° C. for 4 hours.

Cells were then pelleted by centrifugation and supernatant was filter-sterilized and aliquoted for immediate use.

Lytic Activity Assays

*Clostridium perfringens* (CP) strains were grown in fresh BYC (BHI+5 g/L yeast extract+0.5 g/L L-cysteine free base) that was sealed immediately following autoclaving to reduce dissolved oxygen content. Cells were grown at 37° C., sealed and without shaking. After 6 hours, this liquid suspension was used as follows. The suspension was added to a 96-well polystyrene plate such that the final concentration of added supernatant tested was equal to the amounts indicated at a total volume of 200 µL per well in a sterilized 96 well plate.

Results

Using sterilized supernatant, systems producing Lys2 and Lys3 (FIG. 2) were found to have lytic activity against several CP strains (including CP12, CP13, CP26, and CP39). This activity was demonstrated through the reduction of optical density of culture, which correlates to the number of intact bacterial cells which scatter light at wavelength 600 nm (FIG. 3).

The extent of the lysin specificity was demonstrated by the activity response of Lys2 against the panel of CP strains (FIG. 3C). Supernatant from Lys2-secreting (FIG. 3C) or Lys3-secreting (FIG. 3B) *L. lactis* was tested. Filter-sterilized supernatant from Lys2-secreting *L. lactis* was not observed to elicit a response from CP strain CP26, demonstrating strain-level specificity towards targets of interest.

Example 2

A method of using microfluidic co-encapsulation of antimicrobial protein producer and target pathogen (Scanlon et al. Biotechnol. Bioeng. 2014, 111:232-243) adapted for use with *L. lactis* and CP will be used. A mutagenic library is first constructed in LL, 1, mixed with CP in low-gel agarose 2, and encapsulated via a microfluidic device, 3. Droplets are solidified and incubated in-emulsion to allow AMP production, and washed with appropriate fluorescent dyes to indicate activity, 4. Droplets are sorted via fluorescent-activated cell sorting, 5, enriching for droplets with higher total activity. Secretion rate can then be decoupled from per-molecule activity via HPLC for top clones, 6.

A schematic representation of this method is shown in FIG. 4.

Example 3

This Example describes a process for generating lysin catalytic domains.

1. Generation of guide sequence and mutable sequence positions.
   a. Lysin catalytic domain sequences are gathered from a protein sequence database having taxonomic label of an organism against which the lysin is to be generated.
   b. Lysin catalytic domain sequences from (1a) are aligned to generate a multiple sequence alignment using a structurally-guided multiple sequence aligner.
   c. The consensus sequence derived from the multiple sequence alignment of (1b) is acquired and utilized in the following as a seed sequence.
   d. The non-gapped sequence positions of the seed sequence of (1c) with site diversity above some tunable threshold form the set of mutable positions for the following.
2. Generation of a structurally-guided multiple sequence alignment of lysin catalytic domain class
   a. Lysin catalytic domain sequences with either homology to the seed sequence of (1c), or homology with a curated database of lysin catalytic domain family members, are acquired from a protein sequence database having taxonomic label within a phylum of the organism against which the lysin is to be generated.
   b. Lysin catalytic domain sequences from (2a), in addition to the seed sequence of (1c) are aligned to generate a multiple sequence alignment using a structurally-guided multiple sequence aligner.
   c. Non-gapped positions of the seed sequence of (1c) within the multiple sequence alignment of (2b) are used as the basis for statistical model fitting.
3. Generation of a generative model describing reduced multiple sequence alignment of (2c)
   a. Sitewise and pairwise character occurrence frequencies (amino acids, gaps, etc.) corresponding to the reduced multiple sequence alignment of (2c) are computed with phylogenetic bias corrected by one or more of a number of methods.
   b. A statistical model incorporating parameters describing sitewise and pairwise interactions is fit to the bias-corrected character occurrence frequencies of (3a). This statistical model returns a statistical fitness score given a test sequence.
4. Generation of a set of lysin catalytic domain sequences with improved physical properties
   a. An integer programming optimization scheme is utilized to generate sequences with statistical fitness scores greater than the seed sequence of (1c) by allowing in silico mutations at positions of the seed sequence of (1c) as selected in (1d). Additional physical properties can be applied as constraints to the optimization process to steer towards sequences with desired traits, such as net charge.
   b. From the set of sequences generated in (4a) some subsets are selected for experimental verification. Experimental verification may be done in any appropriate context, including catalytic-domain only, and/or using a full-length lysin through the genetic fusion of the generated lysin catalytic domain sequence to the sequence of a cell wall binding domain either from a naturally occurring or a synthetic lysin.

Example 4

This Example describes an exemplary implementation of Example 3, used to generate the lysin catalytic domains Lys2ConCat and Lys2Con20Cat (the sequences of which are provided in Table 2). This Example further describes cloning and expression of these lysin catalytic domains; characterization of thermal stability of Lys2, Lys2Con (a lysin including the Lys2ConCat catalytic domain as well as the cell wall binding domain of Lys2), and Lys2Con20 (a lysin including the Lys2Con20Cat catalytic domain as the cell wall binding domain of Lys2) against CP12; and comparison of Lys2ConCat and Lys2Con20Cat to naturally occurring sequences.

1. Generation of Lys2ConCat and identification of mutable positions
   a. The catalytic domain of Lys2 was utilized as the seed sequence to search for homologous sequences using the Jackhmmer webserver (Finn et al. HMMER web server: 2015 Update. Nucleic Acids Res. 43, W30-W38 (2015)).
b. The following settings yielded 13 sequences:
  i. Iterations: 5
  ii. Sequence Database: UniprotKB
  iii. Taxonomy restriction: *Clostridium perfringens* (taxid: 1502)
  iv. Cut-offs significance E-values
    1. Sequence: 1e-20
    2. Hit: 1e-20
c. Protein sequences from (1a) were aligned using the PROMALS3D server (Pei et al. Nucleic Acids Res. 2008; 36:2295-2300) with standard settings.
d. The consensus sequence of the cluster with sequences closest to Lys2 was computed, yielding Lys2ConCat.
e. Positions of Lys2ConCat with Shannon entropy >0 were designated as mutable positions for later optimization.

2. Acquisition and multiple sequence alignment of Firmicute phylum with sequences homologous to Lys2ConCat.
a. The sequence of Lys2ConCat was utilized as the seed sequence to search for homologous sequences using the Jackhmmer webserver (Finn et al. Nucleic Acids Res. 2015; 43:W30-W38). The following settings yielded 4919 sequences:
  i. Iterations: 5
  ii. Sequence Database: UniprotKB
  iii. Taxonomy restriction: Firmicutes (TAXID: 1239)
  iv. Cut-offs significance E-values
    1. Sequence: 1e-20
    2. Hit: 1e-20
b. Protein sequences from (2a), in addition to Lys2ConCat, were aligned using the PROMALS3D server with standard settings.
c. Non-gapped positions, with respect to Lys2ConCat, of the multiple sequence alignment from (2b) were used for statistical modeling.

3. Parameter determination of a Boltzmann distribution with sequence energy defined by the Potts model
a. A Potts model (Wu, Rev. Mod. Phys. 1982; 54:235) is the simplest model incorporating sitewise and pairwise energy contributions from a character sequence. It is defined as:

$$E(\sigma) = \sum_i h_i(\sigma_i) + \sum_{i<j} J_{i,j}(\sigma_i, \sigma_j)$$

Where $\sigma$ is the character sequence, h is the set of sitewise energy character contributions, and J is the set of pairwise energy character contributions. The parameter set of this function were fitted to the data assuming that character sequence observations follow a Boltzmann distribution:

$$P(\sigma) = \frac{1}{Z}\exp(E(\sigma))$$

Where $P(\sigma)$ is the probability of randomly observing character sequence $\sigma$, and Z is the partition function (the sum of the exponentials of the energies of all possible character sequences). The software package PLMC (Hopf et al. Nat. Biotechnol. 2017, 35(2): 128-135) was used to determine the parameters of this model. The following settings were utilized, the algorithm was run to convergence:
  i. $l_2$ regularization parameters
    1. $\lambda_h$: 0.01
    2. $\lambda_e$: 40.4
  ii. -g (fit only non-gapped positions of Lys2ConCat, which is set at position 1 of the multiple sequence alignment)

4. Generation of sequences starting from Lys2ConCat with increased statistical energy
a. A MATLAB script was written to compute the statistical energy of all single mutations of Lys2ConCat at all positions determined in (1d). The mutation which yielded the highest statistical energy was recorded as a new starting sequence. This process was repeated a total of 20 times to yield sequences Lys2Con1Cat through Lys2Con20Cat.

The sequence with the greatest statistical energy, Lys2Con20Cat was selected for characterization. The sequences of Lys2ConCat and Lys2Con20Cat were genetically fused to the cell wall binding domain of Lys2 to yield the lysins Lys2Con and Lys2Con20, respectively.

Cloning, Expression, and Characterization of Thermal Stability of Lys2, Lys2Con, and Lys2Con20 Against CP12

The full-length amino acid sequences for Lys2 (SEQ ID NO:1), Lys2Con (SEQ ID NO:5), and Lys2Con20 (SEQ ID NO:6) were codon optimized using the Integrated DNA Technologies, Inc. (IDT) Codon Optimization Tool for *Escherichia coli* (available on the world wide web at idtdna.com/CodonOpt) and ordered as a gBlock (Integrated DNA Technologies, Inc., Coralville, Iowa). These genes were Gibson assembled (NEBUILDER Hifi DNA Assembly Kit, New England Biolabs, Inc., Ipswich, Mass.) into a linearized pET expression vector between restriction enzyme sites NdeI and BamHI. This location incorporates a C-terminal GSHHHHHH purification tag in the coding sequence of each lysin.

Assembled plasmids were transformed into NEB T7 Express LysY/Iq cells (New England Biolabs, Inc., Ipswich, Mass.) following the published protocols and plated on lysogeny broth (LB) plates supplemented with 50 µg/mL kanamycin (+kan) and grown at 37° C. overnight.

Fresh colonies were inoculated into 100 mL of LB+kan liquid media and grown, shaking at 250 rpm at 37° C., to an optical density at 600 nm (OD600) of 0.5. Isopropyl β-D-1-thiogalactopyranoside (IPTG) was added to a final concentration of 0.5 mM to induce lysin expression. Induction was carried out shaking at 250 rpm at 37° C. for 2 hours.

Following induction, cultures were placed on ice for 10 minutes. Cells were then pelleted at 3000 g for 10 minutes at 4° C. Culture media was removed and pellets washed 3× with 1 mL ice-cold PBS (137 mM NaCl, 2.7 mM KCl, 10 mM $Na_2HPO_4$, 1.8 mM $KH_2PO_4$, pH 7.4), centrifuged each time at 3000 g for 3 minutes. Cell pellets were then resuspended in lysis buffer (PBS, +3.1 g/L CHAPS, +10 mM imidazole, +1 EDTA-free protease inhibitor cocktail pellet/ 50 mL) and freeze-thawed for 4 cycles (thaw: 30° C., freeze: −20° C.). Suspensions were then centrifuged at 12000 g for 10 minutes and supernatant removed. Supernatant was filter-sterilized for protein purification.

Protein purification was done using a gravity-driven column loaded with 2 mL of HisPur Cobalt Resin (Thermo Fisher Scientific, Waltham, Mass.). Briefly, resin was washed with 4×1 mL of wash buffer (PBS+10 mM imidazole), filter-sterilized lysate was applied, the column was washed with 6×1 mL of wash buffer, and finally the lysins were eluted by 4×1 mL of elution buffer (PBS+150 mM imidazole). Single milliliter fractions were collected at all stages of purification. Lysin elution fraction was determined via lytic activity testing at 37° C.

Fractions containing highest lytic activity for each lysin were applied to Zeba spin desalting column (Thermo Fisher Scientific, Waltham, Mass.) following the manufacturer's protocol with PBS as the equilibration buffer. These solutions were then used for characterization.

For thermal stability testing, 50 µL aliquots of each lysin were distributed into PCR Strip Tubes (Thermo Fisher Scientific, Waltham, Mass.). A C1000 TOUCH Thermocyler (Bio-Rad, Hercules, Calif.) was used to heat shock each sample. Samples were heated to designated temperature for 30 minutes and then 4° C. for 10 minutes. These heat-shocked samples were then used in lytic activity tests.

For lytic activity testing, *Clostrium perfringens* strain ATCC 12916 was grown to an OD600 of 0.5 in fresh BYC (BHI+5 g/L yeast extract+0.5 g/L L-cysteine free base) anaerobically. 180 μL of this culture was applied to 20 μL of heat-shocked protein sample in a sterile, transparent, 96-well polystyrene plate. Plates were then incubated with continuous orbital shaking at 37° C. in a SYNERGY H1 Microplate Reader (BioTek, Winooski, Vt.). OD600 readings were recorded every 2 minutes for 1 hour.

Data for each sampled were fitted to the function:

$$OD600 = \begin{cases} OD600_{0,i} & t < t_{0,i} \\ OD600_{0,i} * \exp(-k_i(t - t_{0,i})) & t_{0,i} \le t \end{cases}$$

This function captures the lytic activity of each lysin and enables comparison of the specific activities, $k_i$. Results are shown in FIG. 5 and Table 1 Table 1 demonstrates the improved stabilities of Lys2Con, and Lys2Con20 relative to Lys2.

TABLE 1

Thermal stabilities of lysins Lys2, Lys2Con, and Lys2Con20. Curves of $k_i$ were fitted to determine the temperature at which lysins lost 50% of their maximum activity ($T_{50}$).

| Construct | $T_{50}$ (C.) |
|---|---|
| Lys2 | 44.9 |
| Lys2Con | 48.4 |
| Lys2Con20 | 53.0 |

Comparison of Lys2ConCat and Lys2Con20Cat to Naturally Occurring Sequences

Naturally occurring sequences with homology to Lys2ConCat and Lys2Con20Cat were gathered using the Jackhmmer webserver (Finn et al. Nucleic Acids Res. 2015; 43:W30-W38). The closest sequence for each was B1R4A5, the catalytic domain for a lysin from *Clostridium perfringens* B str. ATCC 3626. Lys2ConCat and Lys2Con20Cat had sequence identities of 94.1% and 87.1%, respectively, to the catalytic domain of B1R4A5.

With respect to Lys2's catalytic domain, Lys2ConCat and Lys2Con20Cat are 46.2% and 50.8% identical, respectively

TABLE 2

| | |
|---|---|
| SEQ ID NO: 3 (Lys2ConCat) | MEGRNNNNLKGIDVSNWQGNINFKSVKNDGIEVV YIKATEGDYFKDSYAKQNYERAKAEGLKVGFYHF FRPNKNAKDQANYFIDYLNEIGATDYDCKLALDI ETTEGRGAYDLTTMCIEFLEEVRRITNREVVVYT YTSFANNNLDNRLGVYPLWIAHYGVKAPKDNNIW SSWIGFQYSDKGNVAGVSGNCDMNEFKEEIFD |
| SEQ ID NO: 4 (Lys2Con20Cat) | MQSRNNNNLKGIDVSNWQGNINFKSVKNDGIEVV YIKATEGDYFKDSYAKQNYEGAKANGLKVGFYHF FRPNKNAKEQANYFISYLNGIGAKDYDCKLALDI ETTEGLGAYELTTMCIEFLEEVKRLTGKEVVVYT YTSFANNNLDSRLGVYPLWIAHYGVKTPKDNNIW SSWIGFQYSDKGSVAGVSGNCDMNEFTEEILI |
| SEQ ID NO: 5 (Lys2Con) | MEGRNNNNLKGIDVSNWQGNINFKSVKNDGIEVV YIKATEGDYFKDSYAKQNYERAKAEGLKVGFYHF FRPNKNAKDQANYFIDYLNEIGATDYDCKLALDI ETTEGRGAYDLTTMCIEFLEEVRRITNREVVVYT YTSFANNNLDNRLGVYPLWIAHYGVKAPKDNNIW SSWIGFQYSDKGNVAGVSGNCDMNEFKEEIFDIN KESSKVTENKLFSTNARALVALDPRDNPSDNYND LGEIYEGERIQVLAEVCDKEDYLPVKYWKDSEGR ESGKVWIRSKQDYMMIDTYHRVFNVITQLDARYE PSSDSATMGYVKNGERLYVHRTEGNYSLCTYFAG NGYKTAWFTAKYLERI |
| SEQ ID NO: 6 (Lys2Con20) | MQSRNNNNLKGIDVSNWQGNINFKSVKNDGIEVV YIKATEGDYFKDSYAKQNYEGAKANGLKVGFYHF FRPNKNAKEQANYFISYLNGIGAKDYDCKLALDI ETTEGLGAYELTTMCIEFLEEVKRLTGKEVVVYT YTSFANNNLDSRLGVYPLWIAHYGVKTPKDNNIW SSWIGFQYSDKGSVAGVSGNCDMNEFTEEILIIN KESSKVTENKLFSTNARALVALDPRDNPSDNYND LGEIYEGERIQVLAEVCDKEDYLPVKYWKDSEGR ESGKVWIRSKQDYMMIDTYHRVFNVITQLDARYE PSSDSATMGYVKNGERLYVHRTEGNYSLCTYFAG NGYKTAWFTAKYLERI |

The complete disclosure of all patents, patent applications, and publications, and electronically available material (including, for instance, nucleotide sequence submissions in, for example, GenBank and RefSeq, and amino acid sequence submissions in, for example, SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A vector comprising a coding region and a heterologous promoter operably linked to the coding region that encodes an antimicrobial peptide, wherein the antimicrobial peptide comprises catalytic domain of Lys2ConCat (SEQ ID NO:3) or Lys2Con20Cat (SEQ ID NO:4).

2. The vector of claim 1, wherein the heterologous promoter comprises a chloride-inducible promoter or a Pon promoter.

3. The vector of claim 1, wherein the vector comprises an additional coding region that is operably linked to a second promoter, and wherein the additional coding region encodes a modulator protein that regulates the expression of the coding region encoding the antimicrobial peptide.

4. A kit comprising the vector of claim 1.

5. A vector comprising a coding region and a heterologous promoter operably linked to the coding region that encodes an antimicrobial peptide, wherein the heterologous promoter comprises a chloride-inducible promoter, wherein the antimicrobial peptide comprises a catalytic domain of Lys2ConCat (SEQ ID NO:3) or Lys2Con20Cat (SEQ ID NO:4), wherein the coding region encoding the antimicrobial peptide is operably linked to a coding region encoding a signal peptide, and wherein the vector comprises an additional coding region that is operably linked to a second promoter, and further wherein the additional coding region encodes a modulator protein that regulates the expression of the coding region encoding the antimicrobial peptide and is operably linked to the heterologous promoter.

* * * * *

UNITED STATES PATENT AND TRADEMARK OFFICE
CERTIFICATE OF CORRECTION

PATENT NO. : 11,965,190 B2
APPLICATION NO. : 16/645281
DATED : April 23, 2024
INVENTOR(S) : Yiannis John Kaznessis, Seth Ritter and Benjamin Hackel Page 1 of 1

It is certified that error appears in the above-identified patent and that said Letters Patent is hereby corrected as shown below:

In the Claims

Column 41, Line 33, Claim 1, 'comprises catalytic' should read -comprises a catalytic-.

Signed and Sealed this
Twenty-sixth Day of November, 2024

Katherine Kelly Vidal
*Director of the United States Patent and Trademark Office*